US009952231B2

(12) United States Patent
Strongin et al.

(10) Patent No.: US 9,952,231 B2
(45) Date of Patent: Apr. 24, 2018

(54) LYSOPHOSPHATIDIC ACID DETECTION

(71) Applicant: Portland State University, Portland, OR (US)

(72) Inventors: Robert Strongin, Portland, OR (US); Martha Sibrian-Vazquez, Portland, OR (US); Jialu Wang, Portland, OR (US); Lei Wang, Camas, WA (US); Jorge O. Escobedo-Cordova, Portland, OR (US)

(73) Assignee: Portland State University, Portland, OR (US)

( * ) Notice: Subject to any disclaimer, the term of this patent is extended or adjusted under 35 U.S.C. 154(b) by 17 days.

(21) Appl. No.: 14/776,273

(22) PCT Filed: Mar. 14, 2014

(86) PCT No.: PCT/US2014/029025
§ 371 (c)(1),
(2) Date: Sep. 14, 2015

(87) PCT Pub. No.: WO2014/144561
PCT Pub. Date: Sep. 18, 2014

(65) Prior Publication Data
US 2016/0047830 A1  Feb. 18, 2016

Related U.S. Application Data

(60) Provisional application No. 61/790,443, filed on Mar. 15, 2013.

(51) Int. Cl.
*C07D 491/00* (2006.01)
*G01N 33/92* (2006.01)
(Continued)

(52) U.S. Cl.
CPC ......... *G01N 33/92* (2013.01); *C07D 491/107* (2013.01); *C07D 491/22* (2013.01); *C09B 11/24* (2013.01)

(58) Field of Classification Search
CPC ...................................... G01N 33/92
(Continued)

(56) References Cited

U.S. PATENT DOCUMENTS

2010/0291689 A1   11/2010  Strongin et al.

OTHER PUBLICATIONS

Lin Yuan, Weiying Lin, Yueting Yang and Jizeng Song "A fast-responsive fluorescent probe for detection of gold ions in water and synthetic products" Chem. Commun., 2011, 47, 4703-4705.*
(Continued)

*Primary Examiner* — Christopher Adam Hixson
*Assistant Examiner* — Emily R. Berkeley
(74) *Attorney, Agent, or Firm* — Klarquist Sparkman, LLP

(57) ABSTRACT

Embodiments of methods and compounds for isolating and detecting lysophosphatidic acids (LPAs) are disclosed. Kits for performing the methods also are disclosed. LPAs are isolated from biological samples by liquid-liquid extraction followed by solid phase extraction. LPA species may be separated by HPLC, and the separated species may be identified and quantified. Also disclosed are embodiments of compounds capable of universally detecting a plurality of LPA species with substantially equivalent sensitivity. Embodiments of the disclosed compounds are useful for determination of total LPA concentration in a sample comprising a plurality of LPA species without separation of individual LPA species.

13 Claims, 10 Drawing Sheets

(51) Int. Cl.
    *C07D 491/107* (2006.01)
    *C07D 491/22* (2006.01)
    *C09B 11/24* (2006.01)
(58) Field of Classification Search
    USPC .......................................................... 436/71
    See application file for complete search history.

(56) References Cited

OTHER PUBLICATIONS

Elena V. Ivanova and Heidi M. Muchall "Hydrolysis of N-Sulfinylamines and Isocyanates: A Computational Comparison" J. Phys. Chem. A 2007, 111, 10824-10833.*

XiaoLiang Li, YongWu He, Kyung-Il Ahn, and Sung Ik Yang "Development of Fluorescent Turn-On Sensor for Selective Detection of Cu2+ in Aqueous Solution" Bull. Korean Chem. Soc. 2013, vol. 34, No. 6.*

Zhao et al., "A Rhodamine-based $Hg^{2+}$-selective Fluorescent Probe in Aqueous Solution," *Chemical Papers*, 2009, 63(3):261-267.

European Search Report and Written Opinion for related Application No. 147651163.2, dated Aug. 1, 2016, 11 pp.

Huang et al., "A Rhodamine-Based 'Turn-On' Fluorescent Chemodosimeter for $Cu^{2+}$ and its Application in Living Cell Imaging," *Journal of Inorganic Biochemistry* 2011, 105:800-805.

Kishimto et al., "A Novel Colorimetric Assay for the Determination of Lysophosphatidic Acid in Plasma Using an Enzymatic Cycling Method," *Clinica Chimica Acta.* 2003, 333:59-67.

Zhao et al., "A Rhodamine-Based Chromogenic and Fluorescent Chemosensor for Copper Ion in Aqueous Media," *Sensors and Actuators B* 2009, 135(2):625-631.

Baker et al., "Direct Quantitative Analysis of Lysophosphatidic Acid Molecular Species by Stable Isotope Dilution Electrospray Ionization Liquid Chromatography-Mass Spectrometry," *Anal. Biochem.*, 2001, 292:287-295.

Bollinger et al., "Improved Method for the Quantification of Lysophospholipds Including Enol Ether Species by Liquid Chromatography-Tandem Mass Spectrometry," *J. Lipid Res.*, 2010, 51:440-447.

Chen et al., "Determination of Lysophosphatidic Acids by Capillary Electrophoresis with Indirect Ultraviolet Detection," *J. Chromatogr. B. Biomed. Sci. Appl.*, 2001, 753:355-363.

Chen et al., "Isolation and Quantitation of Plasma Lysophosphatidic Acids by Solid-Phase Extraction and Capillary Electrophoresis," *J. of Liquid Chromatography & Related Technologies*, 2002, 25(6):843-855.

Holland et al., "Quantification of Phosphatidic Acid and Lysophosphatidic Acid by HLPC with Evaporative Light-Scattering Detection," *J. Lipid Res.*, 2003, 44:854-858.

Ishida et al., "Effective Extraction and Analysis for Lysophosphatidic Acids and their Precursors in Human Plasma Using Electrospray Ionization Mass Spectrometry," *Mass Spectrometry Society of Japan*, 2005, 53(4):217-226.

Saleem et al., "Selective Fluorescence Detection of $Cu^{2+}$ in Aqueous Solution and Living Cells," *Journal of Luminescence*, 2014, 145:843-848.

Shan et al., "Quantitative Determination of Lysophosphatidic Acid by LC/ESI/MS/MS Employing a Reversed Phase HPLC Column," *J. Chromatogr. B*, 2008, 864:22-28.

Suchocka et al., "New HPLC Method for Separation of Blood Plasma Phospholipids," *Journal of Pharmaceutical and Biomedical Analysis*, 2003, 32:859-865.

Sutphen et al., "Lysophospholipids are Potential Biomarkers of Ovarian Cancer," *Cancer Epidemiol. Biomark. Prev.*, 2004, 13:1185-1191.

Wang et al., "Simple Enrichment and Analysis of Plasma Lysophosphatidic Acids," *Analyst, Author Manuscript*, 2013, 138(22):6852-6859.

Xu et al., "Lysophosphatidic Acid as a Potential Biomarker for Ovarian and Other Gynecologic Cancers," *JAMA*, 1998, 280(8):719-732.

Zhao et al., "An extremely Simple Method for the Extraction of Lysophosopholipids and Phospholipds from Blood Samples," *J. Lipid Res.*, 2010, 51:652-659.

Zuo et al., "A Highly Sensitive Fluorescent Probe for HClO and its Application in Live Cell Imaging," *Journal of Fluorescence*, 2012, 22(5):1201-1207.

Yuan, et al., Supporting Information for "A Fast-Responsive Fluorescent Probe for Detection of Gold Ions in Water and Synthetic Products," *The Royal Society of Chemistry*, 2011, 18 pages.

* cited by examiner

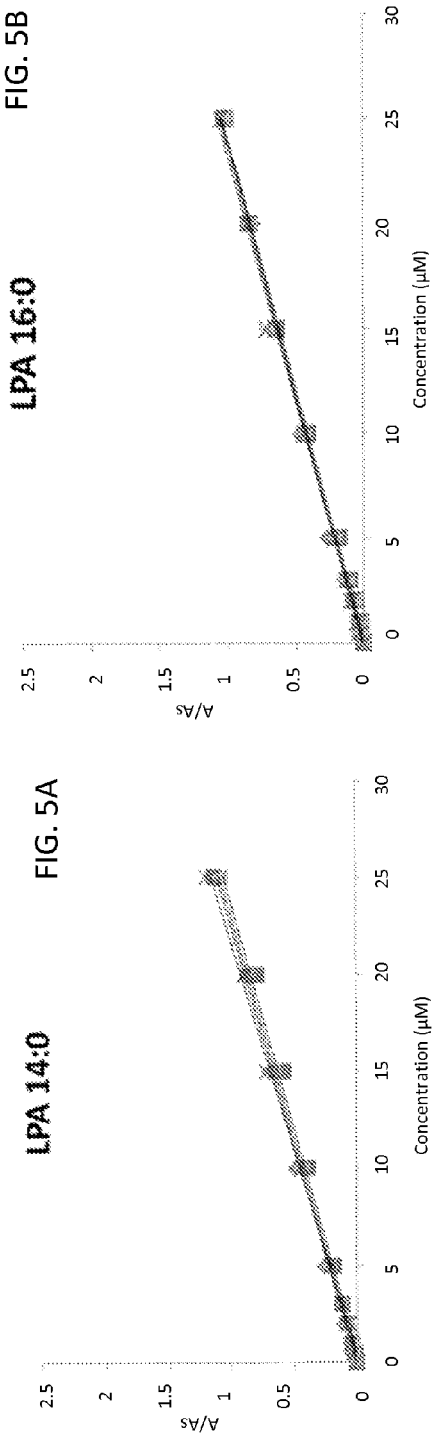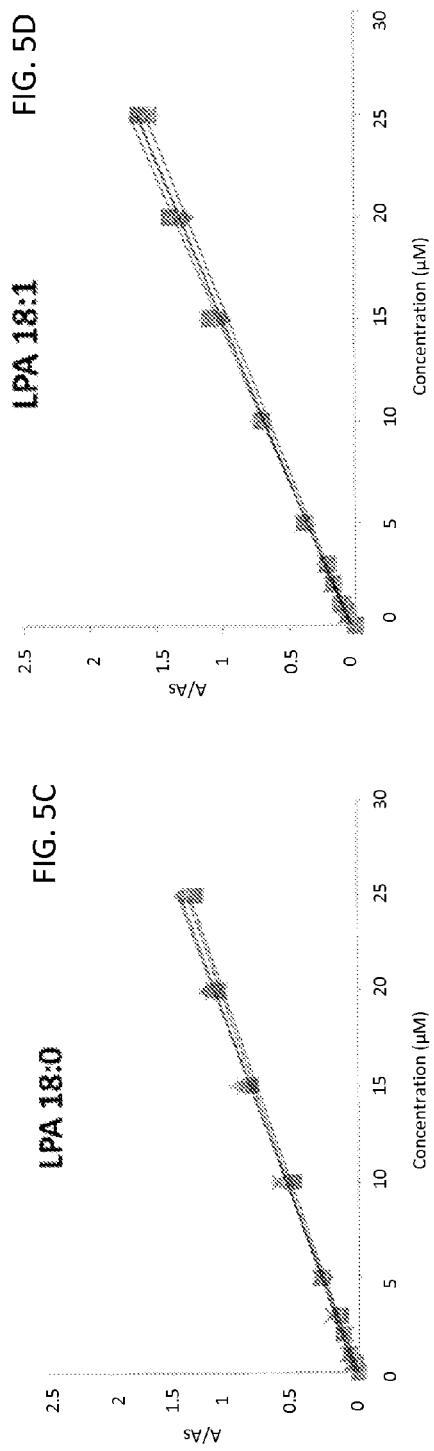

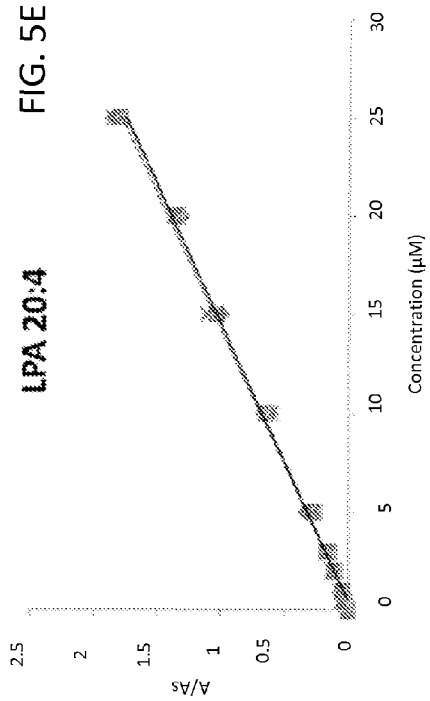
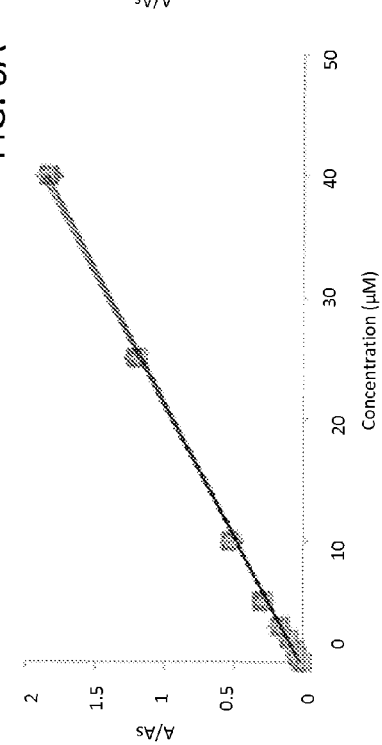
FIG. 5E, FIG. 6A, FIG. 6B

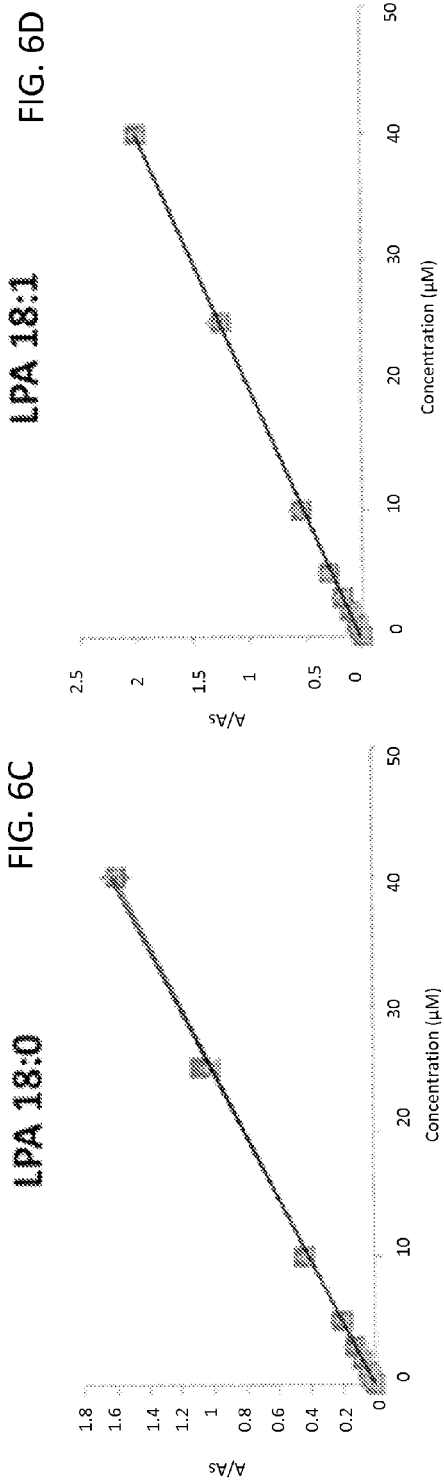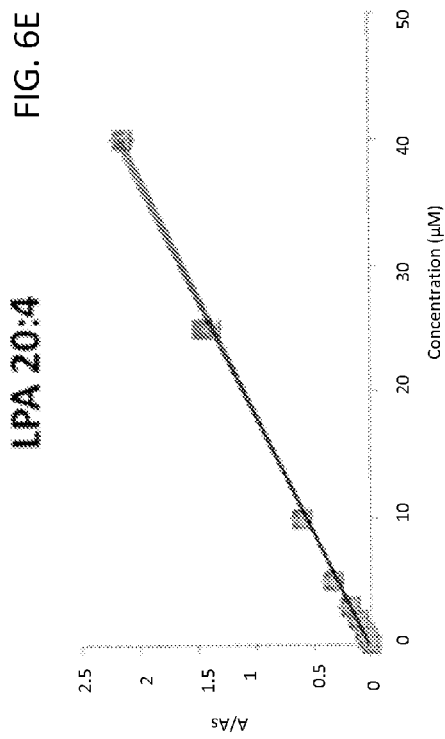
FIG. 6C  FIG. 6D  FIG. 6E

LYSOPHATIDIC ACID DETECTION

CROSS REFERENCE TO RELATED APPLICATIONS

This is the U.S. National Stage of International Application No. PCT/US2014/029025, filed Mar. 14, 2014, which was published in English under PCT Article 21(2), which in turn claims the benefit of U.S. Provisional Application No. 61/790,443, filed Mar. 15, 2013, each of which is incorporated herein in its entirety by reference.

ACKNOWLEDGMENT OF GOVERNMENT SUPPORT

This invention was made with government support under Grant No. RO1 CA136491 awarded by the National Institutes of Health, and Grant No. 0741993, awarded by the National Science Foundation. The government has certain rights in the invention.

FIELD

This disclosure concerns embodiments of methods and compounds for isolating and detecting lysophosphatidic acids. Kits for performing the methods also are disclosed.

BACKGROUND

Lysophosphatidic acid (LPA) is a bioactive phospholipid that stimulates cell proliferation, migration, and survival. Five G-protein-coupled receptors have been identified as specific for LPA. Aberrant LPA production, expression, and signalling have been linked to cancer initiation (e.g., tumorigenesis), progression, angiogenesis, and metastasis. LPA is thought to play a role in a number of cancers, including ovarian cancer and other gynecological cancers. LPA also has been linked to cardiovascular disease (e.g., atherosclerosis, atherothrombosis), platelet aggregation, ischemia perfusion injury, wound healing, neuropathic pain, neuropsychiatric disorders, reproductive disorders, and fibrosis.

In recent years, LPA has been considered as an important and sensitive biomarker of ovarian cancer. Elevated LPA levels in plasma have been found in patients with ovarian cancer. There is evidence suggesting that only certain LPA species (below) are associated with ovarian cancer (Sutphen et al., *Cancer Epidemiol. Biomark. Prev.*, 2004, 13:1185-1191; Xu et al. *JAMA*, 1998, 280:719-732), therefore, quantification of individual LPA species would provide a better way to improve the accuracy of diagnosis. A need also exists for a colorimetric or fluorometric probe capable of detecting equal concentrations of individual LPAs with the same degree of response to more accurately determine total LPA concentration with a single probe.

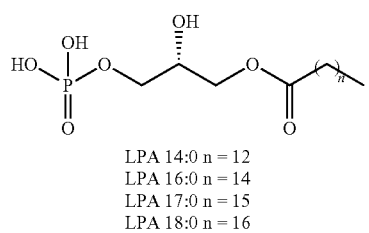

LPA 14:0 n = 12
LPA 16:0 n = 14
LPA 17:0 n = 15
LPA 18:0 n = 16

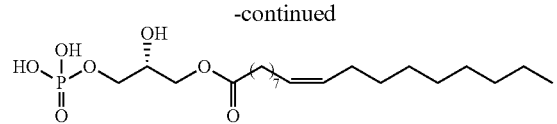

LPA 18:1

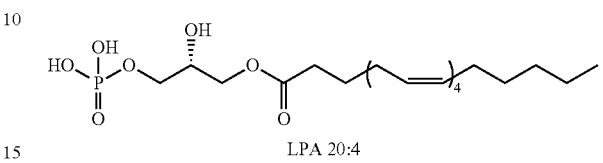

LPA 20:4

Known methods suffer from disadvantages. Xu et al. (*JAMA*, 1998, 280:719-723) used a gas chromatography (GC) method to quantify total LPA plasma levels. Chen et al. (*J. Chromatogr. B. Biomed. Sci. Appl.*, 2001, 753:355-363) used capillary electrophoresis (CE) to quantify individual LPAs with an indirect ultraviolet (UV) for the detection. However, to separate LPA from other lipids before the detection, these and several other studies rely on two-dimensional thin layer chromatography (TLC) as a step, which is time consuming and labor intensive.

Holland et al. (*J. Lipid Res.*, 2003, 44:854-858) used high performance liquid chromatography (HPLC) to separate LPA species and evaporative light-scattering detection (ELSD). This method avoids the two-dimensional TLC step, but LPA elutes at 38 min with a relatively low recovery. LC-MS based methodology has been used to quantify LPAs (Baker et al., *Anal. Biochem.*, 2001, 292:287-295); however, it is not as accurate as LC-MS/MS because LC-MS only determines LPA by detecting the molecular mass ion rather than the parent to daughter ion transitions.

According to some recent studies, LC-MS/MS methods have disadvantages. Shan et al. (*J. Chomatogr. B*, 2008, 864:22-28) found that some unknown compounds in plasma, which produced the same parent-to-daughter ion transition as LPA in a direct flow injection LC-ESI-MS/MS method, could reduce the accuracy of quantification of LPA. Zhao et al. (*J. Lipid Res.*, 2010, 51:652-659) reported lysophosphatidylcholine (LPC) and lysophosphatidylserine (LPS) could lose the choline or serine group to generate LPA-like signals at the ion source. Additionally, phosphatidic acids may be fragmented by enzymes during separation from blood samples and/or fragmented in an ESI detector, in some instances losing one lipid chain and producing a false positive by appearing as LPA. Another disadvantage is that LPAs do not ionize well, and the best results for LPA typically are obtained by running the mass spectrometer in negative ion mode, which can be more technically challenging than the more typical positive ion mode.

SUMMARY

Embodiments of methods and compounds for isolating and detecting lysophosphatidic acids are disclosed. Kits for performing the methods also are disclosed.

Embodiments of compounds suitable for detecting lysophosphatidic acids have a structure according to any one of general formulas I-IV.

With respect to general formula I, $R^1$-$R^6$ independently are H, hydroxyl, thiol, lower alkyl, carboxyalkyl, amino, lower alkoxy, or halogen; $R^7$-$R^{10}$ independently are H, alkyl, acyl, carboxyl, nitro, amino, alkylamino, or —$SO_3H$; $R^{11}$ is N—C(=$R^{13}$)—$NH_2$, N—NH—C(=$R^{13}$)—$NH_2$, N—C($NH_2$)=N—C(=$R^{13}$)—$NH_2$, or N—NH—C($NH_2$)=N—C(=$R^{13}$)—$NH_2$, where $R^{13}$ is O, S, or NH; each $R^{12}$ independently is hydrogen or lower alkyl, or each of $R^1$, $R^2$, $R^5$, and $R^6$ may together with an adjacent $R^{12}$ and N atom form a 6-membered heterocyclic ring; and X is O, S, $CH_2$, NH, or $SiR^{14}$ where $R^{14}$ is H or lower alkyl.

With respect to general formula II, $R^1$-$R^5$, $R^{15}$, $R^{17}$, and $R^{18}$ independently are hydrogen, hydroxyl, thiol, lower alkyl, carboxyalkyl, amino, lower alkoxy, or halogen; $R^{16}$ is —$N(R^{12})_2$; each $R^{12}$ independently is hydrogen or lower alkyl, or each of $R^1$, $R^2$, $R^{15}$, and $R^{17}$ may together with an adjacent $R^{12}$ and N atom form a 6-membered heterocyclic ring; and $R^7$-$R^{10}$, $R^{11}$ and X are as described for general formula I.

With respect to general formula III, $R^2$-$R^5$, $R^{15}$, $R^{17}$, and $R^{19}$-$R^{21}$ independently are hydrogen, hydroxyl, thiol, lower alkyl, carboxyalkyl, amino, lower alkoxy, or halogen; one of $R^{16}$ and $R^{18}$ is hydrogen, hydroxyl, thiol, lower alkyl, carboxyalkyl, amino, lower alkoxy, or halogen, and the other of $R^{16}$ and $R^{18}$ is —$N(R^{12})_2$; each $R^{12}$ independently is hydrogen or lower alkyl, or if $R^{16}$ is —$N(R^{12})_2$, each of $R^{15}$, $R^{17}$, $R^{20}$, and $R^{21}$ may together with an adjacent $R^{12}$ and N form a 6-membered heterocyclic ring; and $R^7$-$R^{10}$, $R^{11}$ and X are as described for general formula I.

With respect to general formula IV, $R^1$-$R^4$, $R^6$, and $R^{22}$-$R^{24}$ independently are hydrogen, hydroxyl, thiol, lower alkyl, carboxyalkyl, amino, lower alkoxy, or halogen; each $R^{12}$ independently is hydrogen or lower alkyl, or each of $R^1$, $R^2$, $R^{23}$, and $R^{24}$ may together with an adjacent $R^{12}$ and N form a 6-membered heterocyclic ring; and $R^7$-$R^{10}$, $R^{11}$ and X are as described for general formula I.

Exemplary compounds include, but are not limited to
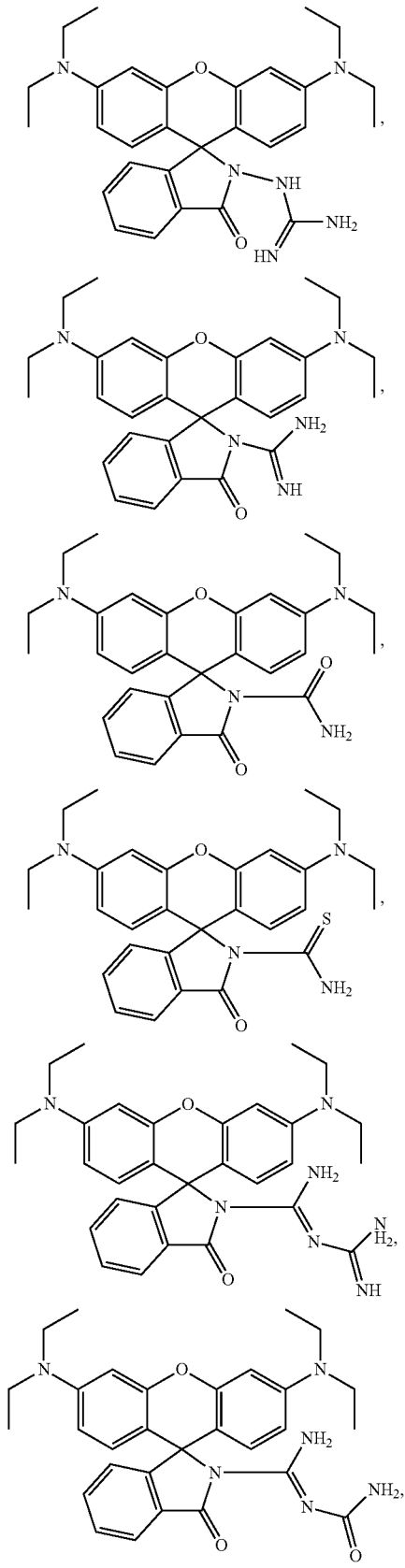
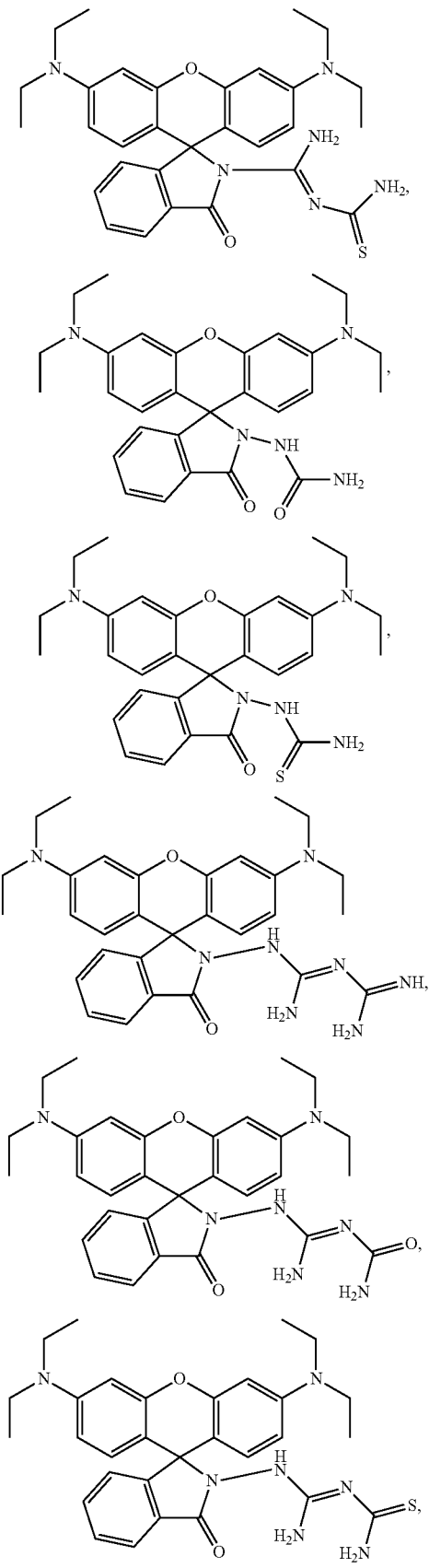

-continued

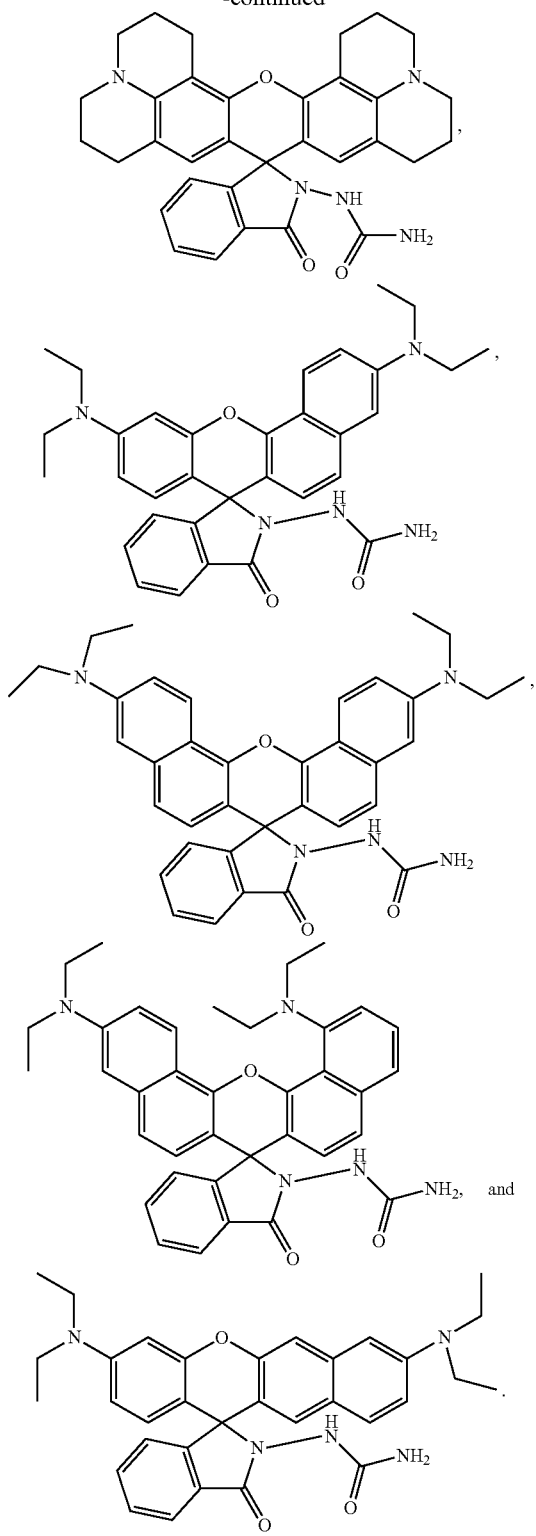

Some embodiments of a method for isolating lysophosphatidic acid species from a plasma or serum sample include obtaining a plasma or serum sample; combining one part plasma or serum sample with five parts solvent comprising methanol and chloroform in a ratio of 2:1 to form a mixture; incubating the mixture at 4° C. for 15-30 minutes; warming the mixture to ambient temperature; separating organic and aqueous layers of the mixture; extracting the aqueous layer with phosphate-buffered saline, pH 7.4 to form an extracted aqueous phase; mixing the extracted aqueous phase with chloroform; separating chloroform from the extracted aqueous phase to form a washed aqueous phase; repeating the steps of mixing the extracted phase with chloroform and separating chloroform from the extracted aqueous phase to form a washed aqueous phase; adding phosphoric acid to the washed aqueous phase to reduce pH to 2, thereby forming an acidified aqueous phase; loading the acidified aqueous phase onto a solid-phase extraction (SPE) cartridge, wherein the SPE cartridge has a C8 stationary phase; flowing water and subsequently chloroform through the SPE cartridge; drying the SPE cartridge; and flowing methanol through the SPE cartridge, thereby eluting lysophosphatidic acid species in methanol from the SPE cartridge. In some embodiments, the method further includes evaporating methanol to form a dry residue comprising lysophosphatidic acid species; and dissolving the dry residue in 9:1 methanol:$H_2O$ to produce an extracted lysophosphatidic acid sample comprising one or more lysophosphatidic acid species.

In some embodiments, a total concentration of lysophatidic acid (LPA) species in the extracted lysophosphatidic acid sample is determined. The sample may be obtained from a subject suspected of being at risk of a condition associated with an aberrant LPA level, the method further comprising determining a risk level for the condition, wherein the risk level is based at least in part on the lysophosphatidic acid concentration. In certain embodiments, the condition is cancer (for example, ovarian cancer), cardiovascular disease, platelet aggregation, ischemia perfusion injury, neuropathic pain, a neuropsychiatric disorder, a reproductive disorder, or fibrosis. Total concentration of LPA can be determined by combining the extracted lysophosphatidic acid sample with a compound according to any one of general formula I-IV in a solvent comprising 2.5-10% dimethylsulfoxide in methanol to form a solution; exposing the solution to a light source; measuring fluorescence intensity of the solution; and determining, based on the fluorescence intensity, the total concentration of lysophosphatidic acid species. In certain examples, the compound is

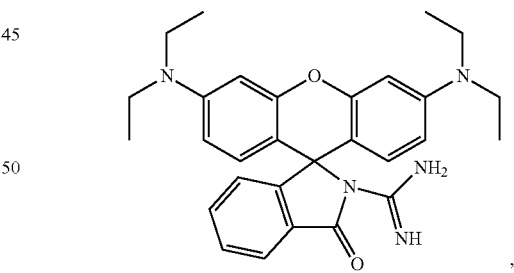

and fluorescence intensity is measured at 570 nm.

In some embodiments, lysophosphatidic acid species in the extracted lysophosphatidic acid sample are separated using a reversed-phase high-performance liquid chromatography (HPLC) column, and individual lysophosphatidic acid species are detected as the separated lysophosphatidic acid species exit the reversed-phase HPLC column. LPA species may be separated using HPLC by flowing the sample into a reversed-phase HPLC column including a C8 stationary phase, and subsequently flowing 16:5 methanol/phosphate buffer (50 mM, pH 2.5) through the reversed-phase HPLC column, thereby forming an eluent comprising lysophosphatidic acid species. Individual LPA species may be detected by combining the eluent with 4-(4-(dihexadecylamino)styryl)-N-methylpyridinium iodide (DiA) as it exits the reversed-phase HPLC column to form a DiA-eluent mixture, flowing the DiA-eluent mixture through a detector, and detecting individual lysophosphatidic acid species by detecting fluorescence of the DiA-eluent mixture as the DiA-eluent mixture flows through the detector.

In certain embodiments, the method further includes identifying an individual lysophosphatidic acid species by comparing an elution time for the individual lysophosphatidic acid species to elute from the reversed-phase HPLC column to elution times for known individual lysophosphatidic acid species, measuring fluorescence intensity of the DiA-eluent mixture, and determining, based on the fluorescence intensity, a concentration of the individual lysophosphatidic acid species. In some examples, the sample is obtained from a subject suspected of being at risk of a condition associated with an aberrant LPA level, and the method includes determining a risk level for the condition, wherein the risk level is based at least in part on an identification of an individual lysophosphatidic acid species, the concentration of the individual lysophosphatidic acid species, or a combination thereof. Exemplary conditions that may be associated with an aberrant LPA level include cancer, cardiovascular disease, platelet aggregation, ischemia perfusion injury, neuropathic pain, a neuropsychiatric disorder, a reproductive disorder, or fibrosis. In certain examples, the condition is ovarian cancer.

Embodiments of kits for detecting and quantifying lysophosphatidic acid include at least one compound according to any one of general formulas I-IV. The kits may further include one or more lysophosphatidic acid species, and/or one or more solid-phase extraction cartridges wherein the stationary phase is C8.

The foregoing and other objects, features, and advantages of the invention will become more apparent from the following detailed description, which proceeds with reference to the accompanying figures.

BRIEF DESCRIPTION OF THE DRAWINGS

FIGS. 5A-5E are a series of calibration curves of LPAs: 14:0—FIG. 5A, 16:0—FIG. 5B, 18:0—FIG. 5C, 18:1—FIG. 5D, and 20:4—FIG. 5E. The curves were obtained using the disclosed HPLC post-column procedure. The area ratio (A/As) is the peak area of the individual LPA divided by the peak area of the internal standard (LPA 17.0).

FIGS. 6A-6E are a series of calibration curves LPAs: 14:0—FIG. 6A, 16:0—FIG. 6B, 18:0—FIG. 6C, 18:1—FIG. 6D, and 20:4—FIG. 6E. The curves were obtained using an LC/ESI/MS/MS method. The area ratio (A/As) is the peak area of the individual LPA divided by the peak area of the internal standard (LPA 17.0).

DETAILED DESCRIPTION

Figure 1:
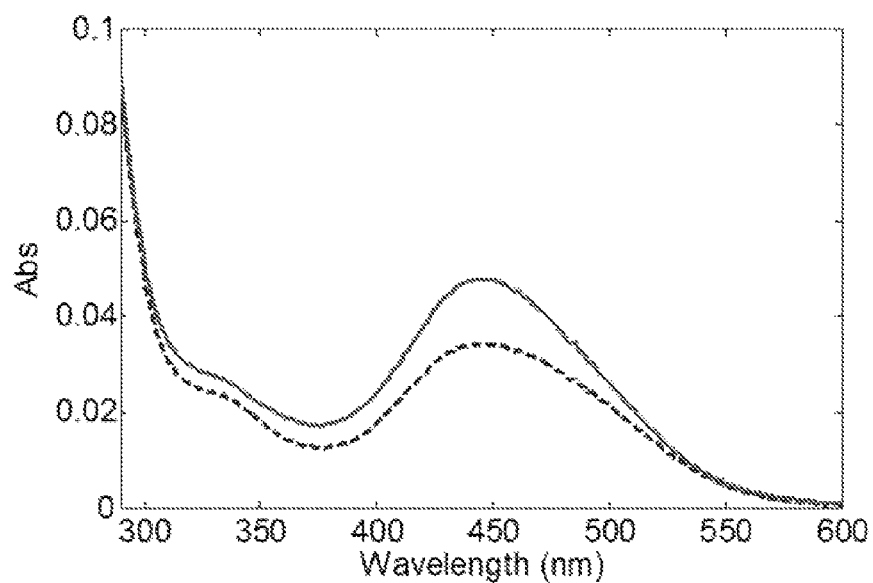
FIG. 1 shows absorbance spectra of an aqueous solution of 3 µM 4-(4-(dihexadecylamino)styryl)-N-methylpyridinium iodide (DiA) in the absence (dashed line) or presence (solid line) of 10 µM lysophosphatidic acid (LPA) 18:0.

Embodiments of methods and compounds for isolating and detecting lysophosphatidic acids (LPAs) are disclosed, along with kits for performing the method. Embodiments of the method include a liquid-liquid and solid-phase extraction process to isolate LPAs in plasma from interfering components. Following extraction, individual LPA species may be separated by HPLC and detected in a fluorometric assay. Alternatively, total LPA may be quantified using embodiments of a fluorescent compound capable of detecting a plurality of LPA species with substantially similar sensitivity.

I. TERMS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Acyl: An organic functional group having the general formula —C(O)R, where R is alkyl, heteroalkyl, haloalkyl, aliphatic, heteroaliphatic, aryl, or heteroaryl.

Alkoxy: A radical (or substituent) having the structure —O—R, where R is a substituted or unsubstituted alkyl. Methoxy (—OCH$_3$) is an exemplary alkoxy group.

Alkyl: A hydrocarbon group having a saturated carbon chain. The chain may be cyclic, branched or unbranched. The term lower alkyl means the chain includes 1-10 carbon atoms.

Alkylamino: An alkyl group where at least one hydrogen is substituted with an amino, mono-substituted amino or di-substituted amino group.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like.

Carboxyalkyl: A functional group with the formula —COOR where R is alkyl.

DiA: 4-(4-(dihexadecylamino)styryl)-N-methylpyridinium iodide

HPLC: high performance (or pressure) liquid chromatography

LPA: lysophosphatidic acid

LPS: lysophosphatidyl serine

PA: phosphatidic acid

PC: phosphatidyl choline

PE: phosphatidylethanolamine

PI: phosphatidyl inositol

Probe: A substance used to detect or identify another substance in a sample.

S1P: sphingosine-1-phosphate

SPE: solid phase extraction

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group.

II. OVERVIEW OF VARIOUS EMBODIMENTS

Embodiments of compounds for detecting lysophosphatidic acids have a structure according to any one of general formulas I-IV. When the compound has general formula I, $R^1$-$R^6$ independently are hydrogen, hydroxyl, thiol, lower alkyl, carboxyalkyl, amino, lower alkoxy, or halogen; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or each of $R^1$, $R^2$, $R^5$, and $R^6$ may together with an adjacent $R^{12}$ and N atom form a 6-membered heterocyclic ring; and X is O, S, CH$_2$, NH, or SiR$^{14}$ where $R^{14}$ is H or lower alkyl. In some embodiments $R^1$-$R^{10}$ are H.

When the compound has general formula II, $R^1$-$R^5$, $R^{15}$, $R^{17}$, and $R^{18}$ independently are hydrogen, hydroxyl, thiol, lower alkyl, carboxyalkyl, amino, lower alkoxy, or halogen; $R^{16}$ is —N($R^{12}$)$_2$; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or each of $R^1$, $R^2$, $R^{15}$, and $R^{17}$ may together with an adjacent $R^{12}$ and N atom form a 6-membered heterocyclic ring; and X is O, S, CH$_2$, NH, or SiR$^{14}$ where $R^{14}$ is H or lower alkyl. In some embodiments, $R^1$-$R^5$, $R^7$-$R^{10}$, $R^{15}$, $R^{17}$, and $R^{18}$ are hydrogen.

When the compound has general formula III, $R^2$-$R^5$, $R^{15}$, $R^{17}$, and $R^{19}$-$R^{21}$ independently are hydrogen, hydroxyl, thiol, lower alkyl, carboxyalkyl, amino, lower alkoxy, or halogen; one of $R^{16}$ and $R^{18}$ is hydrogen, hydroxyl, thiol, lower alkyl, carboxyalkyl, amino, lower alkoxy, or halogen, and the other of $R^{16}$ and $R^{18}$ is —N($R^{12}$)$_2$; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or if $R^{16}$ is —N($R^{12}$)$_2$, each of $R^{15}$, $R^{17}$, $R^{20}$, and $R^{21}$ may together with an adjacent $R^{12}$ and N form a 6-membered heterocyclic ring; and X is O, S, CH$_2$, NH, or SiR$^{14}$ where $R^{14}$ is H or lower alkyl. In some embodiments, $R^2$-$R^5$, $R^7$-$R^{10}$, $R^{15}$, $R^{17}$, and $R^{19}$-$R^{21}$ are hydrogen, one of $R^{16}$ and $R^{18}$ is hydrogen, and the other of $R^{16}$ and $R^{18}$ is —N($R^{12}$)$_2$.

When the compound has general formula IV, $R^1$-$R^4$, $R^6$, and $R^{22}$-$R^{24}$ independently are hydrogen, hydroxyl, thiol, lower alkyl, carboxyalkyl, amino, lower alkoxy, or halogen; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C (=R$^{13}$)—NH$_2$, where R$^{13}$ is O, S, or NH; each R$^{12}$ independently is hydrogen or lower alkyl, or each of R$^1$, R$^2$, R$^{23}$, and R$^{24}$ may together with an adjacent R$^{12}$ and N form a 6-membered heterocyclic ring; and X is O, S, CH$_2$, NH, or SiR$^{14}$ where R$^{14}$ is H or lower alkyl. In some embodiments, R$^1$-R$^4$, R$^{6-10}$, and R$^{22}$-R$^{24}$ are hydrogen.

In any or all of the above embodiments, each R$^{12}$ independently may be methyl or ethyl. In any or all of the above embodiments, X may be oxygen.

In some embodiments, the compound is

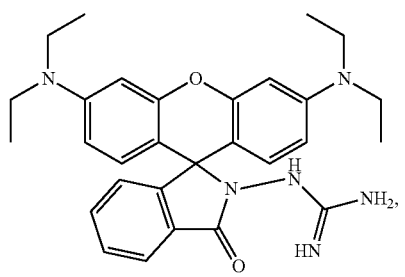

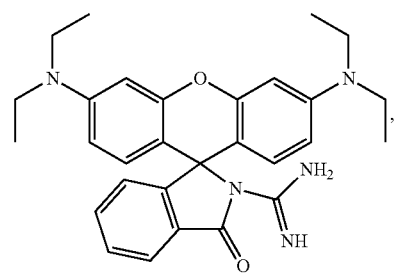

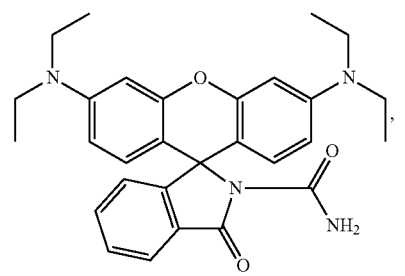

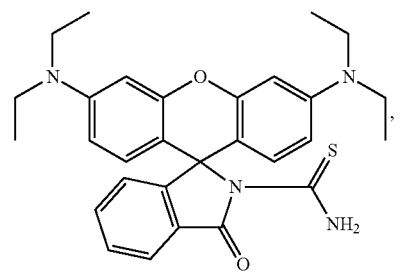

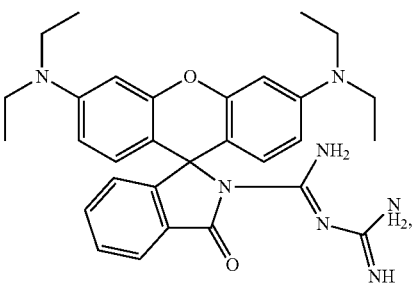

-continued

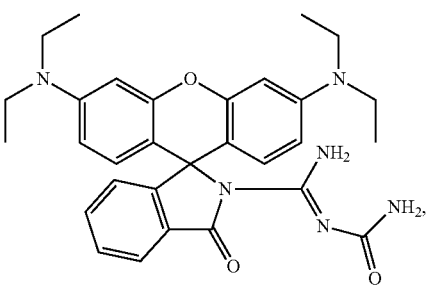

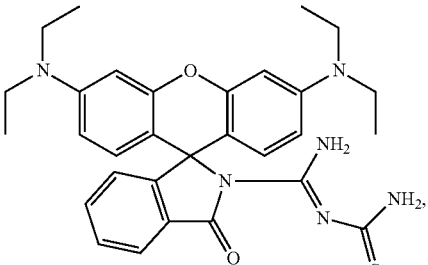

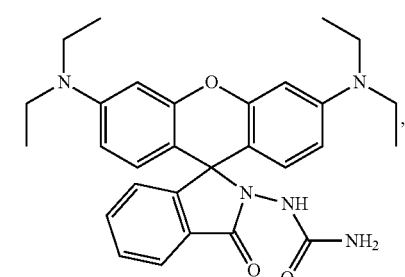

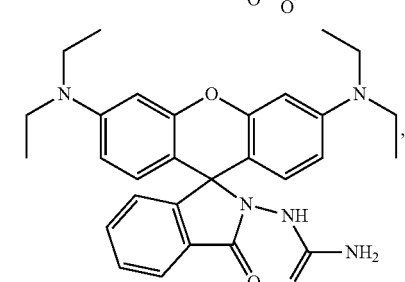

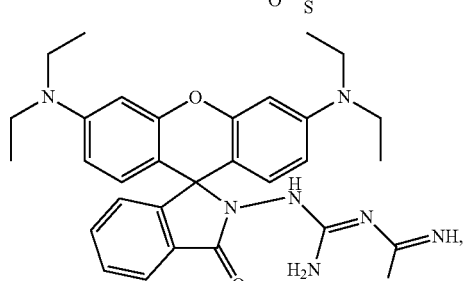

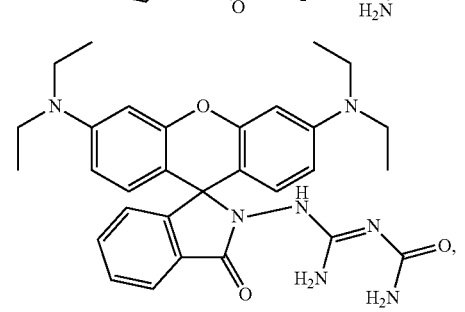

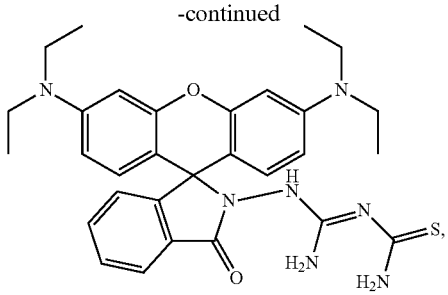

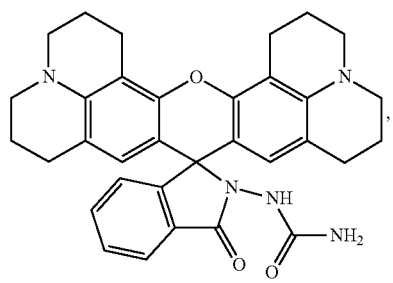

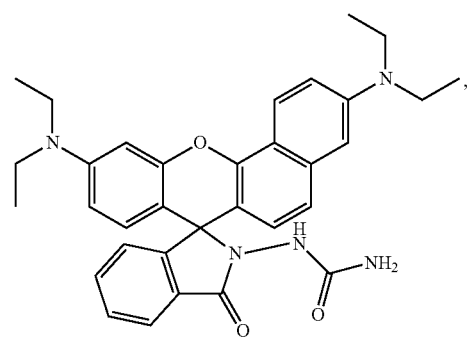

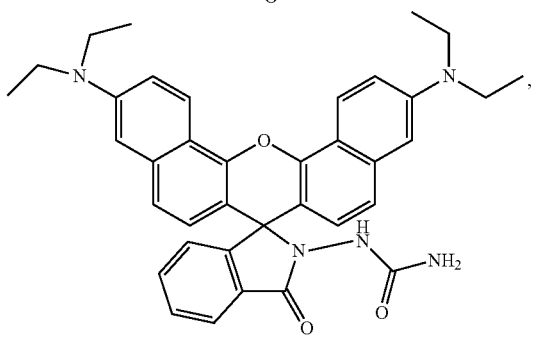

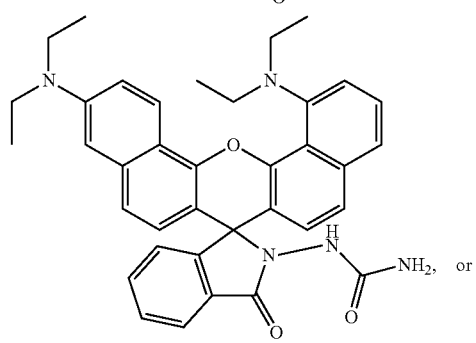

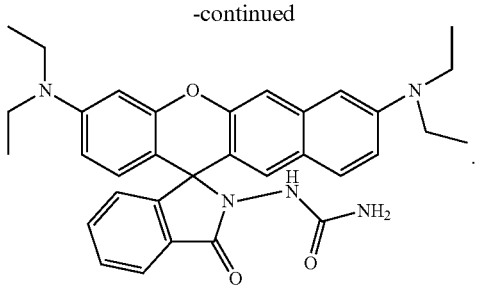

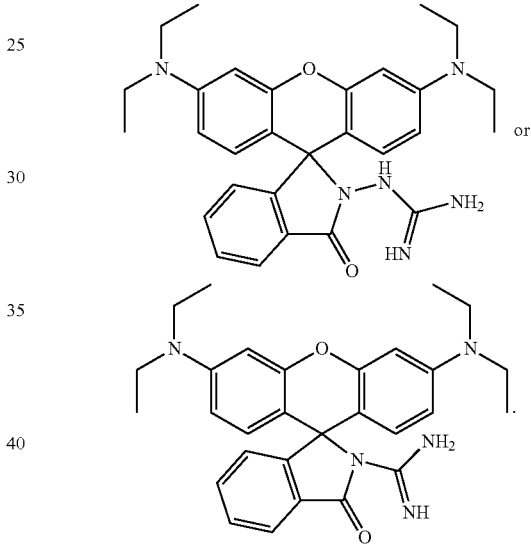

A kit for detecting and quantifying lysophosphatidic acid comprises at least one compound according to any or all of the above embodiments. In some embodiments, the kit further comprises one or more lysophosphatidic acid species. In any or all of the above embodiments, the kit may further comprise one or more solid-phase extraction cartridges wherein the stationary phase is C8. In any or all of the above embodiments, the compound may be A method for quantifying lysophosphatidic acid species comprises combining a sample that may include one or more lysophosphatidic acid species with a compound according to any or all of the above embodiments in a solvent comprising dimethylsulfoxide in methanol to form a solution; exposing the solution to a light source; measuring fluorescence intensity of the solution; and determining, based on the fluorescence intensity, a total concentration of lysophosphatidic acid species in the sample. The solvent may comprise 2.5-10% dimethylsulfoxide in methanol. In some embodiments, the sample is obtained by extracting lysophosphatidic acid species from a plasma or serum sample.

A method for extracting lysophosphatidic acid species includes combining a sample of plasma or serum with a solvent comprising a lower alkyl alcohol and a relatively nonpolar solvent, e.g., chloroform, to form a mixture; separating organic and aqueous layers of the mixture; extracting the aqueous layer with a buffer at neutral pH to form an extracted aqueous phase; mixing the extracted aqueous phase with chloroform; separating chloroform from the extracted aqueous phase to form a washed aqueous phase; adding phosphoric acid to the washed aqueous phase to form an acidified aqueous phase; loading the acidified aqueous phase onto a solid-phase extraction (SPE) cartridge including a stationary phase comprising silica derivatized with hydrocarbon chains; flowing water and subsequently chloroform through the SPE cartridge; drying the SPE cartridge; and flowing a lower alkyl alcohol through the SPE cartridge, thereby eluting lysophosphatidic acid species in the lower alkyl alcohol from the SPE cartridge.

In some embodiments, combining the plasma or serum sample with the solvent comprises combining one part of the plasma or serum sample with five parts of the solvent, the solvent comprising methanol and chloroform in a ratio of 2:1. In any or all of the above embodiments, the method may further comprise incubating the mixture at 4° C. for a period of time; and warming the mixture to ambient temperature before separating the organic and aqueous layers of the mixture. In any or all of the above embodiments, extracting the aqueous layer with a buffer at neutral pH may comprise extracting with phosphate-buffered saline at pH 7.4. In any or all of the above embodiments, the steps of mixing the extracted aqueous phase with chloroform and separating chloroform from the extracted aqueous phase to form a washed aqueous phase may be repeated. In any or all of the above embodiments, sufficient phosphoric acid may be added to the washed aqueous phase to reduce pH to 2. In any or all of the above embodiments, the stationary phase of the SPE cartridge may comprise silica derivatized with octyl chains. In any or all of the above embodiments, the lower alkyl alcohol may be methanol. In any or all of the above embodiments, the method may further include evaporating the lower alkyl alcohol to form a dry residue comprising lysophosphatidic acid species; and dissolving the dry residue in 9:1 methanol:$H_2O$ to produce an extracted lysophosphatidic acid sample comprising one or more lysophosphatidic acid species. In some embodiments, the method further includes determining a total concentration of lysophosphatidic acid species in the extracted lysophosphatidic acid sample.

In some embodiments, the method further includes determining a total concentration of lysophatidic acid species by combining the extracted lysophosphatidic acid sample with a compound as disclosed herein in a solvent comprising dimethylsulfoxide in methanol to form a solution; exposing the solution to a light source; measuring fluorescence intensity of the solution; and determining, based on the fluorescence intensity, the total concentration of lysophosphatidic acid species. The solvent may comprise 2.5-10% dimethylsulfoxide in methanol.

In some embodiments, the compound used for determining a total concentration of lysophosphatidic acid species is

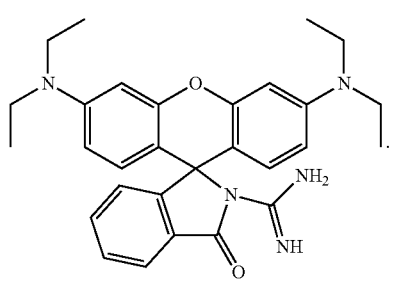 [SMILES: CCN(CC)c1ccc2c(c1)Oc1cc(N(CC)CC)ccc1C21c2ccccc2C(=O)N1C(=N)N]

and fluorescence intensity is measured at 570 nm.

In any or all of the above embodiments, the sample may be obtained from a subject suspected of being at risk of a condition associated with an aberrant LPA level, the method further comprising determining a risk level for the condition, wherein the risk level is based at least in part on the total concentration. In some embodiments, the condition is cancer, e.g., ovarian cancer, cardiovascular disease, platelet aggregation, ischemia perfusion injury, neuropathic pain, a neuropsychiatric disorder, a reproductive disorder, or fibrosis.

In some embodiments, the method further includes separating lysophosphatidic acid species in the extracted lysophosphatidic acid sample using a reversed-phase high-performance liquid chromatography (HPLC) column, and detecting individual lysophosphatidic acid species as the separated lysophosphatidic acid species exit the reversed-phase HPLC column. Separating lysophosphatidic acid species using a reversed-phase high-performance liquid chromatography (HPLC) column may further comprise flowing the sample into the reversed-phase HPLC column, wherein the column has a C8 stationary phase, and subsequently flowing 16:5 methanol/phosphate buffer (50 mM, pH 2.5) through the reversed-phase HPLC column, thereby forming an eluent comprising lysophosphatidic acid species. In any or all of the above embodiments, detecting individual lysophosphatidic acid species may comprise combining the eluent with 4-(4-(dihexadecylamino)styryl)-N-methylpyridinium iodide (DiA) as it exits the reversed-phase HPLC column to form a DiA-eluent mixture; flowing the DiA-eluent mixture through a detector; and detecting individual lysophosphatidic acid species by detecting fluorescence of the DiA-eluent mixture as the DiA-eluent mixture flows through the detector. In some embodiments, the method further comprises identifying an individual lysophosphatidic acid species by comparing an elution time for the individual lysophosphatidic acid species to elute from the reversed-phase HPLC column to elution times for known individual lysophosphatidic acid species, measuring fluorescence intensity of the DiA-eluent mixture, and determining, based on the fluorescence intensity, a concentration of the individual lysophosphatidic acid species.

In any or all embodiments of the above methods, the plasma or serum sample may be obtained from a subject suspected of being at risk of a condition associated with an aberrant LPA level, the method further comprising determining a risk level for the condition, wherein the risk level is based at least in part on an identification of an individual lysophosphatidic acid species, the concentration of the individual lysophosphatidic acid species, or a combination thereof. In some embodiments, the condition is cancer, e.g., ovarian cancer, cardiovascular disease, platelet aggregation, ischemia perfusion injury, neuropathic pain, a neuropsychiatric disorder, a reproductive disorder, or fibrosis.

III. LPA ISOLATION

LPAs are found in plasma and serum. To accurately quantify total LPA and/or to separate, identify, and quantify LPA species, the LPAs must be extracted from the plasma or serum sample and separated from potential interferences, including other phospholipids (e.g., phosphatidic acids, phosphatidyl cholines, lysophophatidyl cholines, lysophosphatidyl serines, phosphatidyl ethanolamine, phosphatidyl inositol, and sphingosine-1-phosphate) that may interfere.

Conventional methods for extracting LPAs insufficiently remove interferences and/or produce poor LPA recoveries. These methods do not adequately prepare LPA samples for quantifying total LPA, or for HPLC separation and subsequent identification/quantification of individual LPA species as disclosed herein. For example, solid phase extraction (SPE) is an accepted method for the removal of potential interferences from biological samples, and has been used for the isolation and enrichment of the different classes of phospholipids. However, SPE alone does not sufficiently remove other phospholipids that can interfere with LPA separation and detection by HPLC. Additionally, although hybrid zirconia and titania support cartridges are known to be useful for recovery of phosphopeptides and removal of phospholipids from biological media, poor recoveries of LPAs were obtained under all evaluated conditions. Because SPE does not sufficiently remove interfering phospholipids, some reported methods include a liquid-liquid extraction step. Typical procedures require plasma acidification prior to extraction. However, evaluation of these methods demonstrated very low LPA recoveries, and insufficient removal of other interferences.

Embodiments of the disclosed method for LPA extraction include a liquid-liquid extraction followed by reversed-phase SPE. Liquid-liquid extraction may be performed with a solvent mixture comprising a lower alkyl alcohol (e.g., methanol, ethanol) and a relatively nonpolar solvent. In some examples, a solvent comprising methanol and chloroform, such as 2:1 MeOH:CHCl$_3$, is mixed with a plasma or serum sample in a ratio of five parts solvent to one part plasma/serum. The combined solvent mixture and plasma/serum sample is incubated at 4° C. for an effective period of time, and then warmed to ambient temperature (e.g., 20° C.). In some embodiments, the effective period of time is at least 15 minutes, such as 15-30 minutes. In certain examples, the effective period of time is 20 minutes. The organic and aqueous layers are separated (e.g., by centrifugation), and the upper aqueous layer is recovered.

Phosphatidic acids are negatively charged at neutral pH. Thus, extraction at neutral pH selectively removes negatively charged LPAs from other neutral and positively charged phospholipids. Accordingly, the upper aqueous layer is extracted with a buffer near physiologic pH, such as phosphate-buffered saline (10 mM, pH 7.4). The aqueous phase is washed with chloroform, and then acidified with phosphoric acid to pH 2.

Reversed-phase SPE separates compounds based on polarity. An SPE column includes a stationary phase (e.g., silica) derivatized with hydrocarbon chains. A solution comprising a mixture of compounds with varying polarities is passed through the column. Compounds with low-polarity are retained on the stationary phase while more polar compounds elute with the solvent. The less polar compounds then are eluted from the stationary phase using a nonpolar solvent. In some embodiments, a C8 SPE cartridge is used. A C8 stationary phase comprises silica functionalized with octyl chains. The cartridge may be preconditioned with a polar solvent, or series of polar solvents, such as methanol followed by water. The acidified aqueous phase from the liquid:liquid extraction is loaded onto the cartridge. The cartridge is washed first with water to remove any polar species, and then with chloroform. The SPE cartridge is dried, with a nitrogen stream, to remove residual chloroform, and LPAs subsequently are eluted with a lower alkyl alcohol, e.g., methanol. The most hydrophobic species are retained on the stationary phase.

In certain examples, isolating LPA includes obtaining a plasma or serum sample, e.g., from a subject having, or being at risk of developing, a condition associated with aberrant LPA levels. The plasma or serum sample is combined with a solvent comprising 2:1 methanol:chloroform; the combined mixture includes one part plasma or serum sample and five parts solvent. In certain examples, 0.8 mL of plasma or serum sample and 4 mL of solvent are used. The mixture is thoroughly mixed, e.g., by vortexing at 2,000 rpm for 30 seconds. The mixture is then incubated at 4° C. for 20 minutes, warmed to ambient temperature, and the aqueous and organic layers are separated, e.g., by centrifugation at 2000 rpm for 10 minutes. The upper aqueous layer is extracted with 2 mL phosphate-buffered saline (10 mM, pH 7.4) by vortexing at 2000 rpm for 30 seconds. The aqueous phase is separated and washed twice with chloroform (1.33 mL). After each washing, the layers are separated, and the chloroform layer is discarded. The washed aqueous phase is acidified to pH 2 with phosphoric acid. The acidified aqueous phase is then loaded on a C8 SPE cartridge that has been preconditioned with 6 mL of methanol, followed by 3 mL of water. After the sample is loaded onto the cartridge, the cartridge is rinsed with 3 mL water, and then 1 mL chloroform. The cartridge then is dried, e.g., with a nitrogen stream. LPAs are eluted from the dried cartridge with 4 mL methanol. The eluted LPAs may be dried, and reconstituted in 9:1 methanol:water for further analysis, such as HPLC separation.

IV. LPA SPECIES HPLC SEPARATION AND POST-COLUMN DETECTION

Following solid-phase extraction of LPAs from plasma or serum, the LPA species are separated using HPLC and then detected. A fluorescent probe 4-(4-(dihexadecylamino) styryl)-N-methylpyridinium iodide (DiA, below) is used as a post-column reagent for the fluorescent detection and quantification of phospholipids. DiA fluorescence can be detected with an excitation wavelength of 450-470 nm and an emission wavelength of 570-590 nm. Embodiments of the disclosed method, including the initial LPA extraction, are capable of separating and quantifying at least six individual LPA species. In some embodiments, six individual LPA species at physiological levels in plasma can be separated and detected in 15 minutes. Compared to conventional LC-MS methods, embodiments of the disclosed method are more practical and reliable since the method is not prone to ionization-related issues and is relatively inexpensive for routine analysis.

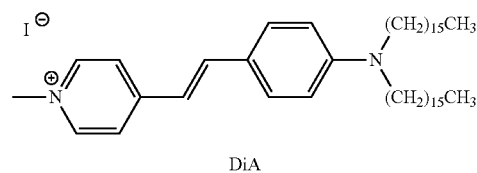

DiA

HPLC can be used to separate LPA species. Desirably, HPLC separation will provide complete separation of LPA species with minimal peak broadening and a reasonable separation time (e.g., less than 20 minutes). It was determined that reversed-phase HPLC would be suitable. An extensive evaluation of solvent systems determined that common solvent mixtures (methanol/water, acetonitrile/water) did not adequately resolve LPA species. Phosphate buffer was found to provide the best results. Complete separation of LPA species depends, at least in part, on buffer concentration and pH, and optimal separation was obtained with 50 mM phosphate buffer, pH 2.5. In some examples, LPAs were eluted using a 16:5 mixture of methanol:phosphate buffer (50 mM, pH 2.5).

Several reversed-phase columns were evaluated, and C8-based columns were found to provide superior results. A shorter column (i.e., 50 mm vs. 100 mm) minimized peak broadening and provided a desirably short separation time of ~15 minutes. Peak width is a result-effective variable, with narrower peaks providing better separation (less diffusion and overlap of adjacent peaks) and allowing a lower detection limit due to less dilution of the LPA species.

In some embodiments, the LPA species are detected with DiA. DiA is mixed with the eluent exiting the HPLC column (e.g., via a 3-way connector or mixing tee), and the mixture then flows into a fluorescence detector. As individual LPA species exit the column, become mixed with DiA, and flow into the detector, fluorescence increases and the LPA species are detected. DiA concentration and flow rate are both result-effective variables. Both concentration and flow rate are selected to provide an optimal signal-to-noise ratio with a relatively low fluorescence background. In some examples, a 10 µM aqueous DiA solution with a flow rate of 0.60 mL/minute to 0.65 mL/minute (e.g., 0.62 mL/min.) was used. The lower limit of LPA detection was determined as being the amount of an LPA species that produced a signal-to-noise ratio of 3:1. Embodiments of the disclosed method have a lower limit of detection of ≤0.3 µM, such as ≤0.2 µM or ≤0.1 µM. Solutions of known LPA species can be used to determine retention times for identification of peaks.

LPA species can be quantified by first preparing calibration curves using standard solutions of LPA species at known concentrations. Because DiA fluorescence intensity varies for different LPA species at equivalent concentrations, a calibration curve is prepared for each species. Once the calibration curves are prepared, the concentrations of LPA species in an unknown sample can be determined by comparing fluorescence intensity of each LPA species to the respective calibration curve.

In certain embodiments, 20 µL of extracted LPAs in 9:1 methanol:water is injected onto a C8-based HPLC column (e.g., LUNA™ C8 column, 50×2 mm, 3 µm) and eluted with a solvent comprising 16:5 methanol:phosphate buffer (50 mM, pH 2.5) at a flow rate of 0.32 mL/minute. The distal end of the HPLC column is coupled to one inlet of a mixing tee. An aqueous DiA solution (10 µM) is coupled to a second inlet of the mixing tee and set to a flow rate of 0.62 mL/minute. The combined eluent and DiA solution flows through the outlet of the mixing tee and into a fluorescence detector. Fluorescence is measured using an excitation wavelength of 450 nm and an emission wavelength of 570 nm. As each LPA species elutes from the HPLC column and flows through the detector, an increase in fluorescence is observed.

Identification and quantification of individual LPA species can be used to evaluate a subject's risk level of having, or developing, a condition correlated with aberrant LPA levels. In some embodiments, a subject's risk of having or developing an LPA-related condition is proportional to the concentration of one or more LPA species in the subject's blood. For example, elevated levels of plasma LPA have been found in patients with ovarian cancer. Other conditions associated with elevated LPA levels include other cancers (e.g. breast cancer, gynecological cancers), cardiovascular disease, platelet aggregation, ischemia perfusion injury, wound healing, neuropathic pain, neuropsychiatric disorders, reproductive disorders, and fibrosis. Some conditions are correlated with elevated levels of only certain LPA species. Thus, determining the presence and concentration of individual LPA species may improve diagnosis accuracy.

V. COMPOUNDS AND METHODS FOR TOTAL LPA DETECTION

In some conditions, total LPA concentration may be predictive of a subject's risk of having, or developing, a condition associated with aberrant LPA levels. Thus, it is desirable to have a single probe capable of detecting a plurality of LPA species with equivalent sensitivity.

Fluorogenic probes commercially available for phospholipid detection can be classified as fluorescent lipid analogs. Phospholipid detection is based on the enhancement or quenching of fluorescence emission intensity as a result of aggregation/de-aggregation between the phospholipid and the fluorophore. Since this non-specific process is dependent on the type, length and number of alkyl chains present in the phospholipid; these probes are not useful for total phospholipid analysis since the fluorescence intensity will vary from phospholipid to phospholipid. Thus, if a plurality of phospholipids is present, the concentration cannot be accurately determined based upon the total fluorescence.

Embodiments of the disclosed fluorogenic compounds are based on a rhodamine B framework, and are functionalized with a guanidine, biguanidine, guanylurea, or guanylthiourea group. Upon interaction of the guanidine, biguanidine, guanylurea, or guanylthiourea group with the phosphate group of a phospholipid, electrostatic interactions will alter the compound's fluorescence.

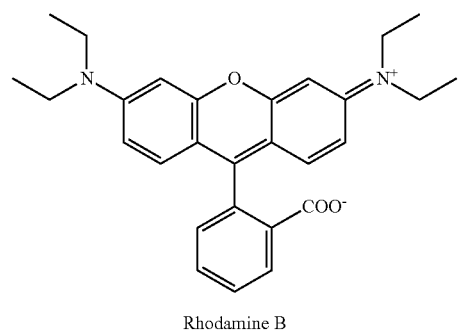

Rhodamine B

Some embodiments of the disclosed compounds have a structure according to general formula I.

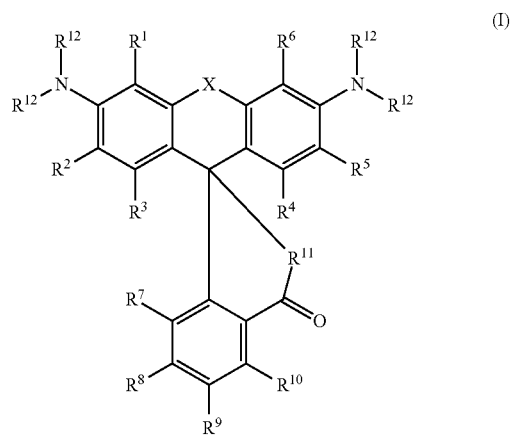

In general formula I, $R^1$-$R^6$ independently are hydrogen, hydroxyl, thiol, lower alkyl, carboxyalkyl, amino, lower alkoxy, or halogen; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or each of $R^1$, $R^2$, $R^5$, and $R^6$ may together with an adjacent $R^{12}$ and N atom form a 6-membered heterocyclic ring; and X is O, S, CH$_2$, NH, or SiR$^{14}$ where $R^{14}$ is H or lower alkyl. In some embodiments, each $R^{12}$ independently is methyl or ethyl. In certain embodiments, $R^1$-$R^{10}$ are hydrogen.

In some embodiments, the disclosed compounds have a structure according to general formula II.

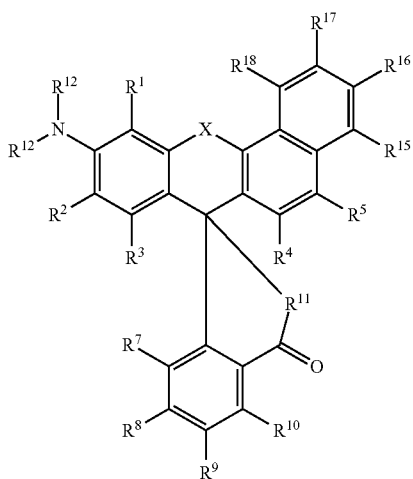

(II)

In general formula II, $R^1$-$R^5$, $R^{15}$, $R^{17}$, and $R^{18}$ independently are hydrogen, hydroxyl, thiol, lower alkyl, carboxyalkyl, amino, lower alkoxy, or halogen; $R^{16}$ is N($R^{12}$)$_2$; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or each of $R^1$, $R^2$, $R^{15}$, and $R^{17}$ may together with an adjacent $R^{12}$ and N atom form a 6-membered heterocyclic ring; and X is O, S, CH$_2$, NH, or SiR$^{14}$ where $R^{14}$ is H or lower alkyl. In some embodiments, each $R^{12}$ independently is methyl or ethyl. In certain embodiments, $R^1$-$R^5$, $R^7$-$R^{10}$, $R^{15}$, $R^{17}$, and $R^{18}$ are hydrogen.

Some embodiments of the disclosed compounds have a structure according to general formula III.

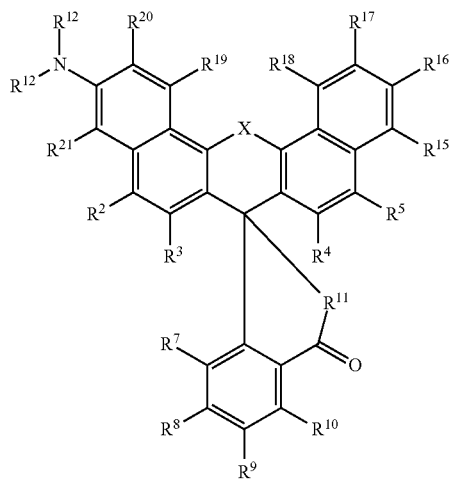

(III)

In general formula III, $R^2$-$R^5$, $R^{15}$, $R^{17}$, and $R^{19}$-$R^{21}$ independently are hydrogen, hydroxyl, thiol, lower alkyl, carboxyalkyl, amino, lower alkoxy, or halogen; one of $R^{16}$ and $R^{18}$ is hydrogen, hydroxyl, thiol, lower alkyl, carboxyalkyl, amino, lower alkoxy, or halogen, and the other of $R^{16}$ and $R^{18}$ is —N($R^{12}$)$_2$; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or if $R^{16}$ is —N($R^{12}$)$_2$, each of $R^{15}$, $R^{17}$, $R^{20}$, and $R^{21}$ may together with an adjacent $R^{12}$ and N form a 6-membered heterocyclic ring; and X is O, S, CH$_2$, NH, or SiR$^{14}$ where $R^{14}$ is H or lower alkyl. In some embodiments, each $R^{12}$ independently is methyl or ethyl. In certain embodiments, $R^2$-$R^5$, $R^7$-$R^{10}$, $R^{15}$, $R^{17}$, $R^{19}$-$R^{21}$, and one of $R^{16}$ and $R^{18}$ are hydrogen.

Some embodiments of the disclosed compounds have a structure according to general formula IV.

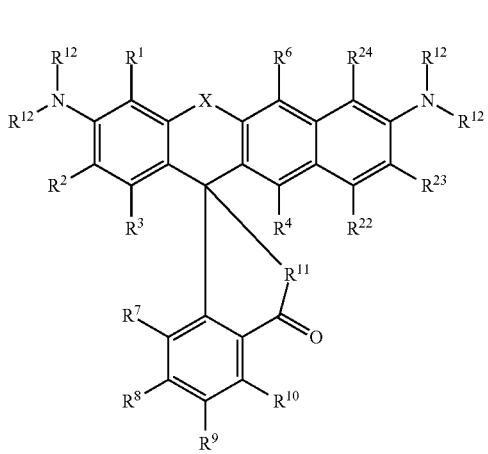

(IV)

In general formula IV, $R^1$-$R^4$, $R^6$, and $R^{22}$-$R^{24}$ independently are hydrogen, hydroxyl, thiol, lower alkyl, carboxyalkyl, amino, lower alkoxy, or halogen; $R^7$-$R^{10}$ independently are hydrogen, alkyl, acyl, carboxyl, nitro, amino, alkylamino, or —SO$_3$H; $R^{11}$ is N—C(=$R^{13}$)—NH$_2$, N—NH—C(=$R^{13}$)—NH$_2$, N—C(NH$_2$)=N—C(=$R^{13}$)—NH$_2$, or N—NH—C(NH$_2$)=N—C(=$R^{13}$)—NH$_2$, where $R^{13}$ is O, S, or NH; each $R^{12}$ independently is hydrogen or lower alkyl, or each of $R^1$, $R^2$, $R^{23}$, and $R^{24}$ may together with an adjacent $R^{12}$ and N form a 6-membered heterocyclic ring; and X is O, S, CH$_2$, NH, or SiR$^{14}$ where $R^{14}$ is H or lower alkyl. In some embodiments, each $R^{12}$ independently is methyl or ethyl. In certain embodiments, $R^1$-$R^4$, $R^6$, $R^7$-$R^{10}$, and $R^{22}$-$R^{24}$ are hydrogen.

Exemplary compounds include, but are not limited to:
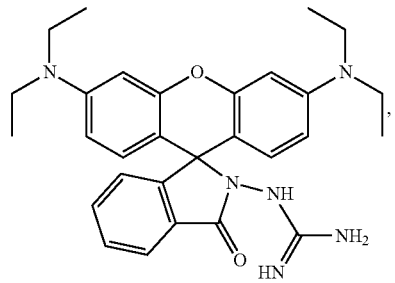
GRBI
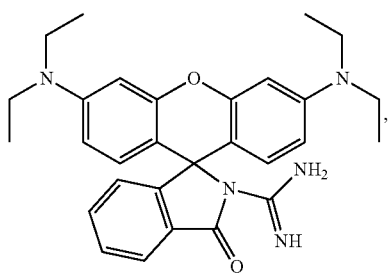
GRBII
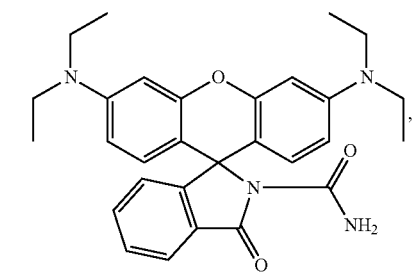
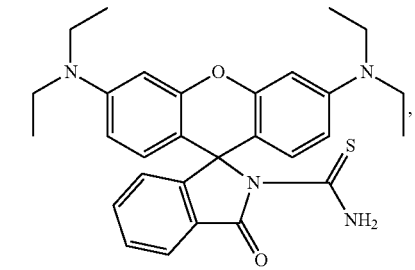
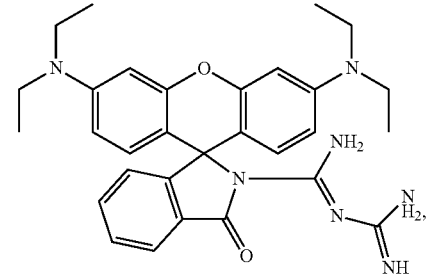
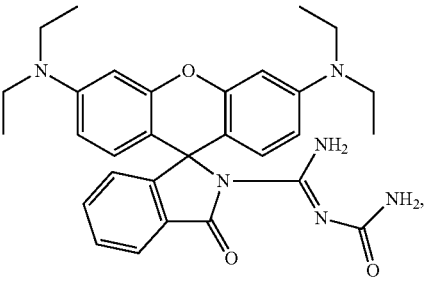
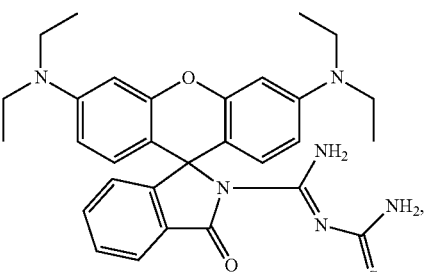
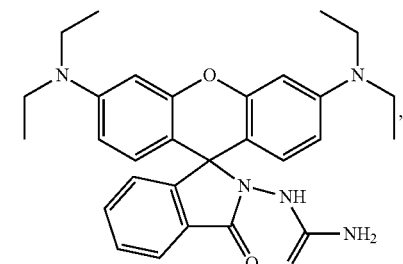
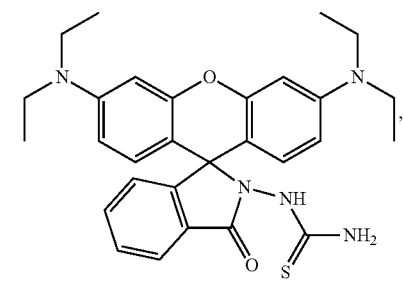
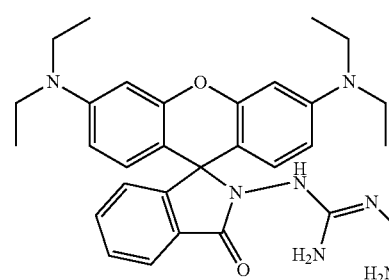
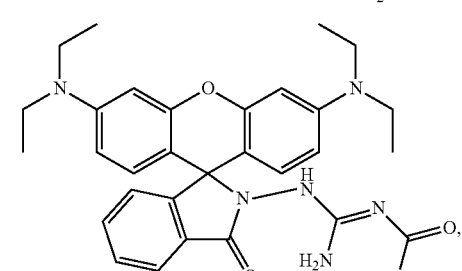

-continued

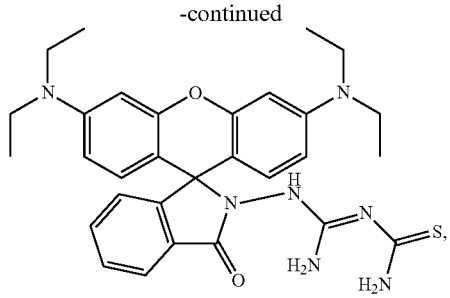

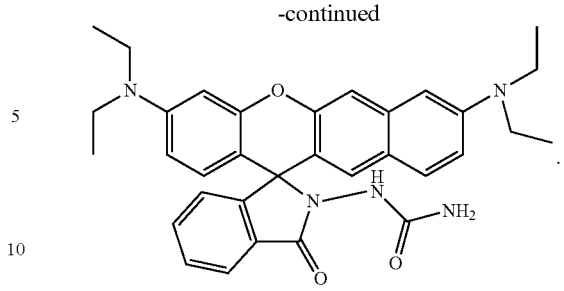

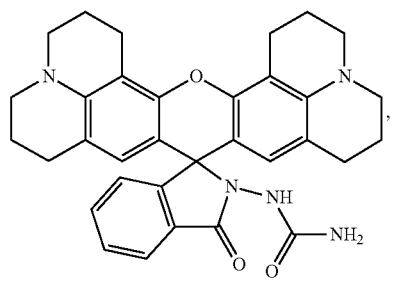

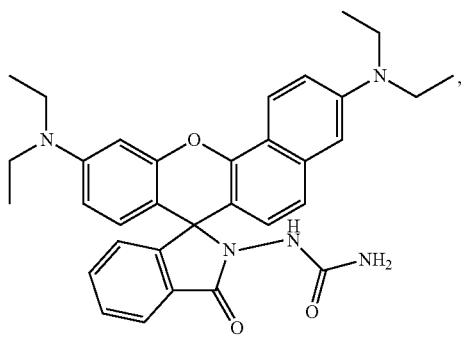

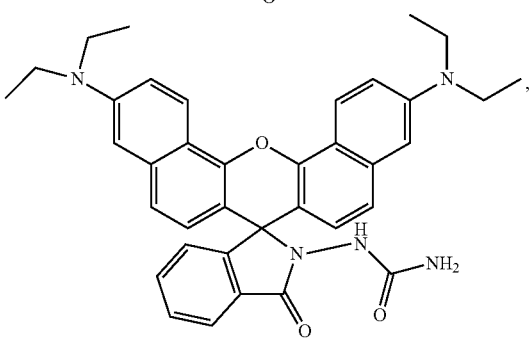

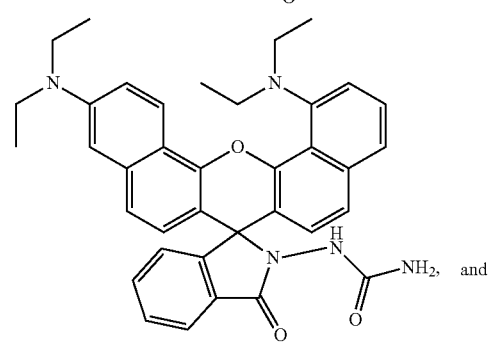

and

Compounds according to general formulas I-IV include a lactam ring. When the lactam ring is present, the compound is non-fluorescent. However, when the guanidine group interacts with the phosphate group of lysophosphatidic acid, the bond between $R^{11}$ and the upper 3-ring portion of the structure is broken and the lactam ring opens, thereby altering electrostatic interactions within the compound, and rendering the compound fluorescent.

Some embodiments of compounds according to general formulas I-IV are suitable for universal detection of LPA. In other words, substantially the same fluorescence intensity is obtained at a given LPA concentration irrespective of the particular LPA species present. In some embodiments, when the compound is combined with a sample comprising isolated LPAs, the fluorescence intensity is stable over time. For example, the fluorescence intensity may remain substantially constant for at least 10 minutes, at least 20 minutes, or at least 30 minutes.

A sample that may include one or more LPAs is combined with a compound according to any one of general formulas I-IV in a suitable solvent to form a solution. The solution is exposed to a light source, and LPAs, if present, are detected by detecting fluorescence of the solution at a suitable wavelength. For GRBI and GRBII, an excitation wavelength of 550 nm and an emission wavelength of 570 nm may be used. Suitable solvents include those in which both the compound and the LPAs are soluble. Exemplary solvents include chloroform/DMSO mixtures, such as mixtures comprising 2.5-10% (v/v) DMSO. In certain examples, a sample potentially comprising LPAs is combined with a compound according to any one of general formulas I-IV in a solvent comprising 9:1 chloroform:DMSO. Desirably, the compound is present in an excess amount compared to the LPAs.

In some embodiments, the LPA sample is obtained from a biological sample, e.g., plasma or serum obtained from a subject at risk of having, or developing, a condition correlated with aberrant LPA levels. The LPA sample may be prepared from the biological sample using liquid-liquid extraction followed by SPE extraction as described herein.

A calibration curve can be prepared by combining a compound according to any one of general formulas I-IV with a series of samples having known concentrations of one or more LPA species and measuring the fluorescence intensity of each solution. The concentration of LPA in an unknown sample is determined by combining the unknown sample with the compound, measuring the fluorescence intensity, and comparing the fluorescence intensity to the calibration curve.

VI. SAMPLE COLLECTION AND STORAGE

Embodiments of the methods and compounds disclosed herein are suitable for detecting LPAs in plasma and serum samples. Blood samples are stored at 4° C. before processing, such as for 4-8 hours. An anti-coagulant, e.g., EDTA, is added to plasma samples before storage to prevent platelet aggregation and inhibit cation-dependent lipid enzymatic processes. Platelets are removed from plasma samples before storage; otherwise, the platelets may undergo lysis and release additional amounts of LPA into the sample. The stored samples are centrifuged to remove blood cells before analysis. In some embodiments, the sample is centrifuged at 1750×g for 15 minutes at ambient temperature (~20° C.). The supernatant (plasma or serum) is stored in low-binding siliconized tubes or glass tubes. (Baker et al., *JAMA, J. Am. Med. Assoc.*, 2002, 287:3081-3082; Xiao et al., *Ann. N. Y. Acad. Sci.*, 2000, 905:242-259; Xu et al., *JAMA, J. Am. Med. Assoc.*, 1998, 280:719-723; Yi et al., *Functional Lipidomics*, CRC Press, 2005, 125-146). Desirably, sufficient blood is collected to provide a plasma or serum sample with a volume of at least 3.5 mL, or at least 5 mL, such that the sample may be evaluated in triplicate.

VII. KITS

Kits for total LPA quantification are also a feature of this disclosure. Embodiments of the kits include at least one compound according to any one of general formulas I-IV and suitable for detecting LPAs extracted from a sample (e.g., plasma or serum). In some embodiments, the probe is GRBI or GRBII. In some embodiments, the kits also include one or more solvents suitable for detecting fluorescence of LPAs when combined with the probe. For example, the kit may include chloroform and dimethylsulfoxide, or a solution comprising 9:1 chloroform:DMSO.

The kits also may include one or more containers, such as a disposable test tube or cuvette, in which the detection can be performed. In certain embodiments, the compound may be premeasured into the one or more containers, and the detection is subsequently performed by adding the solvent(s) and test sample to the container).

The kits may further include instructions for performing the detection and, optionally, instructions for extracting LPAs from a biological sample. The kits also may include one or more solid-phase extraction cartridges suitable for the extraction, e.g., one or more C8 SPE cartridges. In certain embodiments, the kit further includes one or more control samples of LPAs. The control samples may be provided in solid form or in solution.

VIII. EXAMPLES

Materials

All the lysophosphatidic acids including 1-myristoyl-2-hydroxy-sn-glycero-3-phosphate (LPA 14:0), 1-palmitoyl-2-hydroxy-sn-glycero-3-phosphate (LPA 16:0), 1-heptadecanoyl-2-hydroxy-sn-glycero-3-phosphate (LPA 17:0), 1-stearoyl-2-hydroxy-sn-glycero-3-phosphate (LPA 18:0), 1-oleoyl-2-hydroxy-sn-glycero-3-phosphate (LPA 18:1) and 1-arachidonoyl-2-hydroxy-sn-glycero-3-phosphate (LPA 20:4) were purchased from Avanti Polar Lipids (Alabaster, Ala., USA). 4-(4-(Dihexadecylamino)-styryl)-N-methyl-pyridinium iodide (DiA) was purchased from AnaSpec (Fremont, Calif., USA). HPLC grade MeOH was purchased from Fisher Scientific. Ultra-pure water was obtained from a MILLI-Q™ ultra-pure water system. Phosphoric acid and monosodium phosphate were purchased from Sigma-Aldrich (St. Louis, Mo., USA). Waters OASIS™ HLB (3 cc, 60 mg, 30 µm) SPE cartridges were purchased from Waters Corporation (Milford, Mass., USA).

Rhodamine B, Rhodamine B Base, 1,3-bis-Boc-2-methyl-2-thiopseudourea, Sodium methoxide solution (0.5 M), and 1,3-bis(tert-butoxycarbonyl)guanidine were purchased from Aldrich. Anhydrous potassium carbonate and trifluoroacetic acid were purchased from Fisher Scientific. Mercury(II) chloride was purchased from Acros Organics. LPA sodium salts were purchased from Avanti. Silica gel was purchased from Sorbent Technologies. All chemicals were used as received without further purification.

Instrumentation:

Fluorescence measurements were performed on a Cary Eclipse fluorescence spectrophotometer and absorption spectra on a Cary 50 UV-Vis spectrophotometer (Agilent Technologies).

The HPLC system consists of a 1525 binary HPLC delivery system, a 2475 multi lambda fluorescence detector (Waters). A LUNA™ C8 (50×2 mm, 3 µm) column connected to a guard cartridge with 2.0 to 3.0 mm internal diameters was used for all the separations (Phenomenex). The reagent is pumped by a reagent manager (Waters). The post-column reagent and HPLC system are mixed and delivered to the detector by a metal mixing tee. The data was collected and processed with the EMPOWER™ software suite (Waters).

For LC/ESI/MS/MS, LPAs were separated in an ACCELA® UPLC system (Thermo Fisher, San Jose, Calif.) and detected in an LTQ-ORBITRAP™ XL DISCOVERY® instrument (San Jose, Calif., USA), equipped with an ESI ion mass source. The data was collected in negative mode and processed with the XCALIBUR® software suite.

NMR spectra were recorded on a Bruker spectrometer in $CDCl_3$ and DMSO-$d_6$ solutions, and chemical shifts were reported in δ units.

High-resolution ESI/MS spectra were recorded on a ThermoElectron LTQ-ORBITRAP™ DISCOVERY® instrument equipped with an ESI ion mass source.

Example 1

Extraction of LPAs

Several solid supports were initially evaluated in LPA control mixtures containing LPA 14:0, 16:0, 17:0, 18:0, 18:1 and 20:4. Despite the common use of hybrid Zr and $TiO_2$ support cartridges for the recovery and enrichment of phosphopeptides and removal of phospholipids from biological media, little or no LPA recovery was obtained under all the different conditions tested.

Reversed-phase SPE materials provided better results. Three different commercial reversed-phase C8 SPE cartridges, including Waters (SEP-PAK® Plus C-8 cartridge, 200 mg, 37-55 µm), Supelco (DISCOVERY® DSC-8 cartridge, 3 mL, 500 mg, 50 µm) and Waters (OASIS™ HLB cartridge 3 mL, 60 mg, 30 µm) were evaluated. From the evaluated commercial cartridges, the OASIS™ HLB cartridge proved to be the best in terms of LPA recoveries.

A liquid-liquid extraction prior to the SPE procedure was desirable to remove other phospholipids that may interfere with the detection of LPAs. Typical procedures reported in the literature involve acidification of plasma prior to a liquid-liquid extraction. However, this procedure gave very low LPA recoveries and removal of other interferences.

Control of pH was discovered to have an important role in selective removal of interferences. Because phosphatidic acids have a $pKa_1$=2.9 and $pKa_2$=7.5 (Kooijman et al., *Biochemistry*, 2005, 44:17007), they are negatively charged at neutral pH. Thus performing liquid-liquid extraction at this condition separated neutral and positively charged phospholipids from the negatively-charged LPAs.

Acidification of the aqueous phase at pH 5.0, 4.0, 3.0 and 2.5 in the SPE step was evaluated, revealing that lower pH during SPE improved LPA enrichment. The use of MeOH as the final solvent allowed the selective elution of LPAs, leaving behind the most hydrophobic species. The best recoveries (74-100%) were obtained at pH 2.5.

Recovery tests were performed. Three concentrations including 0.25 µM, 3 µM and 5 µM of each LPA species mixed in PBS buffer were tested after liquid-liquid extraction and SPE. Each buffered LPA solution was mixed with 4 mL of MeOH:CHCl$_3$ 2:1 and vortexed at 2000 rpm for 30 seconds. The mixture was incubated at 4° C. for 20 minutes and warmed to room temperature. The mixture was then centrifuged at 2000 rpm for 10 minutes, and the upper layer was separated and extracted with 2 mL PBS (10 mM, pH 7.4) by vortexing at 2000 rpm for 30 seconds. The aqueous phase was separated and washed with 1.33 mL CHCl$_3$ twice, then acidified to pH 2 with concentrated H$_3$PO$_4$. An SPE cartridge was preconditioned with 6 mL of MeOH, followed by 3 mL of H$_2$O. The sample was loaded to the cartridge and rinsed with 3 mL of H$_2$O and then with 1 mL of CHCl$_3$. The SPE cartridge was dried by applying a N$_2$ stream, and LPAs were eluted with 4 mL of MeOH. The MeOH was evaporated, and the residue was reconstituted in 0.16 mL of MeOH:H$_2$O 9:1. Samples (20 µL) obtained from the SPE purification step were injected and eluted with a mixture of MeOH:phosphate buffer (50 mM, pH 2.5) 16:5 through a C8 column. The end of the column was connected to a mixing tee allowing contact with the post-column reagent solution (DiA, 10 µM). The flow rate of the mobile phase was set to 0.32 mL/min and 0.62 mL/min for the post-column reagent. Each concentration was done three times.

As shown in Table 1, the recoveries of LPA 14:0, LPA 16:0, LPA 17:0, LPA 18:0, LPA 18:1 and LPA 20:4 are 93.45%, 94.15%, 85.14%, 76.87%, 76.86% and 73.79%, respectively. In addition, the contribution of other phospholipids that have been identified to be present in human plasma was evaluated. These other phospholipids can result in potential false positives for LPAs. In general, it is known that phospholipids are prone to either chemical or enzymatic hydrolysis. Phosphatidic acids (PAs) hydrolyze producing their corresponding LPAs, adding to the apparent LPA concentrations. Due to the acidic conditions in which the LPA solid phase extraction was carried out, control experiments were performed to measure at what extent PAs were hydrolyzed. The results demonstrated that none of PA 14:0, PA 16:0, PA 18:0 or PA 18:1 was hydrolyzed. Phosphatidyl cholines (PCs) represent the major components of biological membranes and are also prone to hydrolysis producing the corresponding lysophosphatidyl cholines (LPCs). It was determined that PCs do not hydrolyze under our enrichment conditions. On the other hand, LPCs and lysophosphatidyl serines (LPSs) were found to be potential interferences. While LPC interference was removed by doing three consecutive liquid-liquid extractions instead of one, the presence of lysophosphatidyl serines (LPS) was determined not to be significant, since they are usually found at a much lower concentration than LPAs. Other phospholipids including phosphatidyl ethanolamine (PE), phosphatidyl inositol (PI) and SIP were also evaluated and found not to be interferences.

TABLE 1

| LPA Species | Measured by HPLC-post column | | Measured by HPLC-MS/MS | |
|---|---|---|---|---|
| | Recovery in control (%) | RSD (%) | Recovery in control (%) | RSD (%) |
| 14:0 | 93.45 | 4.8 | 93.67 | 2.9 |
| 20:4 | 73.79 | 4.3 | 76.60 | 1.2 |
| 16:0 | 94.15 | 5.4 | 95.72 | 4.6 |
| 18:1 | 76.86 | 4.9 | 77.55 | 1.7 |
| 17:0 | 85.14 | 3.8 | 84.97 | 4.6 |
| 18:0 | 76.87 | 4.4 | 73.14 | 2.4 |

Example 2

HPLC and Post-Column Procedure for LPA Separation and Detection

Figure 2:
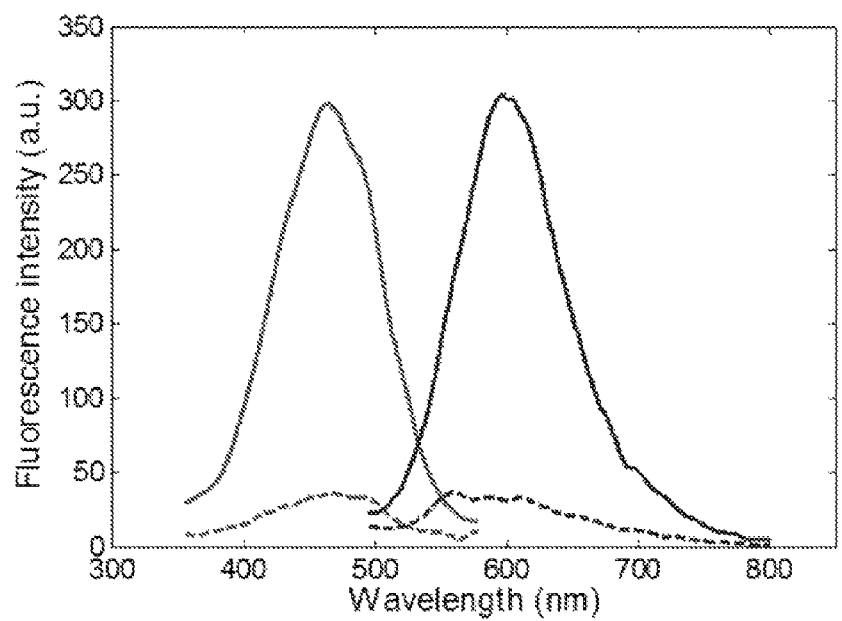
FIG. 2 shows fluorescence emission spectra of 3 µM DiA in the absence (dashed line) or presence (solid line) of 10 µM LPA 18:0 ($\lambda_{ex/em}$=470/590 nm).

LPA Detection:

Fluorescent probes used for post-column detection of phospholipids, typically rely on non-covalent interactions of the phospholipid with the probe's supramolecular assemblies that are solvent dependent. Examples of these probes include 2,5-bis-2-(5-tert-Butyl)benzoxazolylthiophene (BBOT) and 1,6-diphenyl-1,3,5-hexatriene (DPH). Evaluation of BBOT and DPH produced higher fluorescence emission enhancement for double-chain phosphatidic acids (PA) compared to single-chain analogues (lysophosphatidic acids, LPAs) investigated herein. Another class of fluorescent probes with amphiphilic properties was also evaluated. Although 10-N-nonyl acridine orange (NAO) has been proposed for the analysis of specific phospholipids like cardiolipin (CL), it did not exhibit a significant spectral response for LPA. Extending the alkyl chain of NAO to an octadecyl chain did not improve LPA detection. Evaluation of the amphiphilic cyanine type probe 4-(4-(dihexadecylamino)styryl)-N-methylpyridinium iodide (DiA) gave the most promising results for LPA detection. As shown in FIG. 1, 3 µM DiA shows an increase in absorbance at 440-450 nm in the presence of 10 µM LPA 18:0. DiA (3 µM) exhibits weak fluorescence emission at 590 nm (excitation: 470 nm) in aqueous medium, and upon addition of 10 µM LPA 18:0, an increase in fluorescence emission is observed (FIG. 2).

Figure 3:
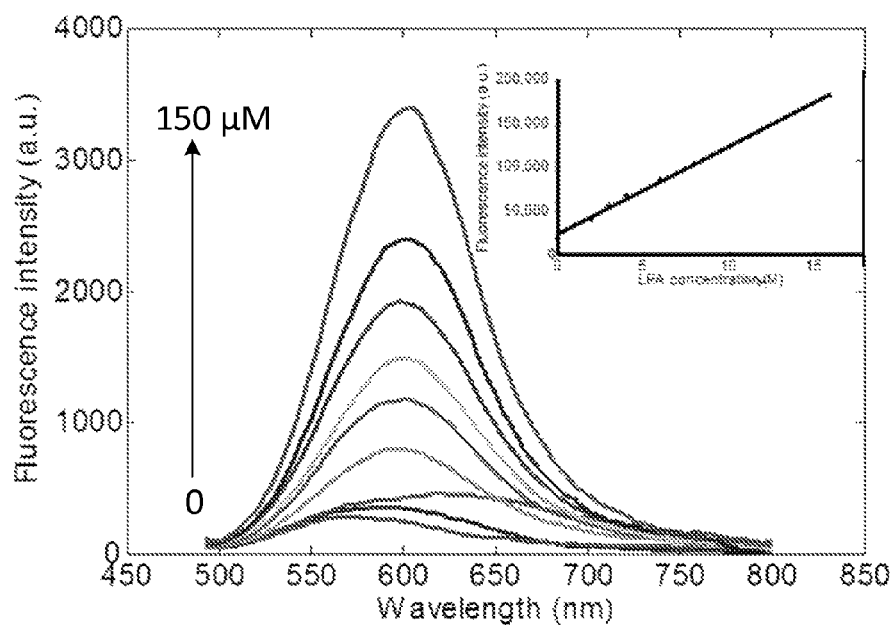
FIG. 3 shows emission spectra and a calibration curve (inset) of 2.67 µM DiA upon titration with LPA (18:0).

To determine the linear response of DiA in the presence of LPA, an initial evaluation using LPA (18:0) as the model compound was carried out using direct fluorescence spectrometry. Solutions of increased concentrations (0, 6.25, 12.5, 18.75, 25, 37.5, 50, 75, 100 and 150 µM) of LPA (18:0) were prepared in a mixture of MeOH:CHCl$_3$ 1:1. To avoid aggregation of the lipids, films for each concentration tested were prepared by evaporation under an Ar stream, and the films were reconstituted in MeOH. Choline chloride (final concentration 6.4 mM) was added before mixing with DiA (final concentration 2.67 µM) aqueous solution. Emission spectra for each solution were collected from 480 to 800 nm exciting at 470 nm (FIG. 3). As shown in the inset of FIG. 3, the plot of maximum fluorescence emission versus concentration demonstrated a good linear relationship ($R^2=0.997$) between the fluorescence intensity and LPA (18:0) concentrations ranging from 1 to 16 µM.

LPA Separation:

The common solvent mixtures (MeOH/H$_2$O, MeCN/H$_2$O) used for reversed-phase chromatography were not able to resolve individual LPA species. From the various buffer systems evaluated, it was found that phosphate buffer gave better separation and peak shapes. LPA species separation was dependent on buffer pH and concentration. Optimal resolution was achieved with 50 mM phosphate buffer pH 2.5. The use of mobile phase modifiers, including trifluoroacetic acid (TFA) and choline chloride were also evaluated. Only choline chloride gave suitable separation, however, it increased significantly both the time of analysis and column back pressure.

Several reversed phase columns were evaluated. The best results were obtained from C8-based columns. The DISCOVERY® BIO™ wide pore C8 column (100×2.1 mm, 3 μm) was able to separate all the LPAs well, but caused very high pressure and limited optimization of the composition/flow rate of mobile phase, achieving only long analysis times (>40 minutes). The LUNA™ C8 column (50×2 mm, 3 μm) allowed an increased flow rate, thereby producing sharper peaks and significantly reducing the analysis time (~15 minutes). The length of the tubing was also important for achieving good peak resolution and lower limits of detection. Shorter tubing minimized peak broadening (and potential overlapping) due to diffusion as the LPA species flowed through the column. The effect of temperature was also studied when working with the longer tubing, with no appreciable change in the range 20-60° C.

Detection of Separated LPA Species:

The 3-D mode feature in the Waters 2475 fluorescence detector was used to determine suitable excitation and emission wavelengths for detection. The detector gain was set to 100. The acquisition mode was set to excitation scanning mode (330-530 nm) while keeping the emission wavelength constant (570 nm).

Solutions of DiA with concentrations ranging from 3 to 20 μM were tested and compared. Among them, 10 μM showed optimal signal-to-noise ratio with a relatively low fluorescence background. Reagent flow rates from 0.15 to 0.70 mL/min were tested and compared. Higher flow rates resulted in higher signal to noise ratios; however, they also induced a weaker signal due to excessive dilution of the sample. The optimal reagent flow rate was found to be 0.62 mL/min.

Figure 4:
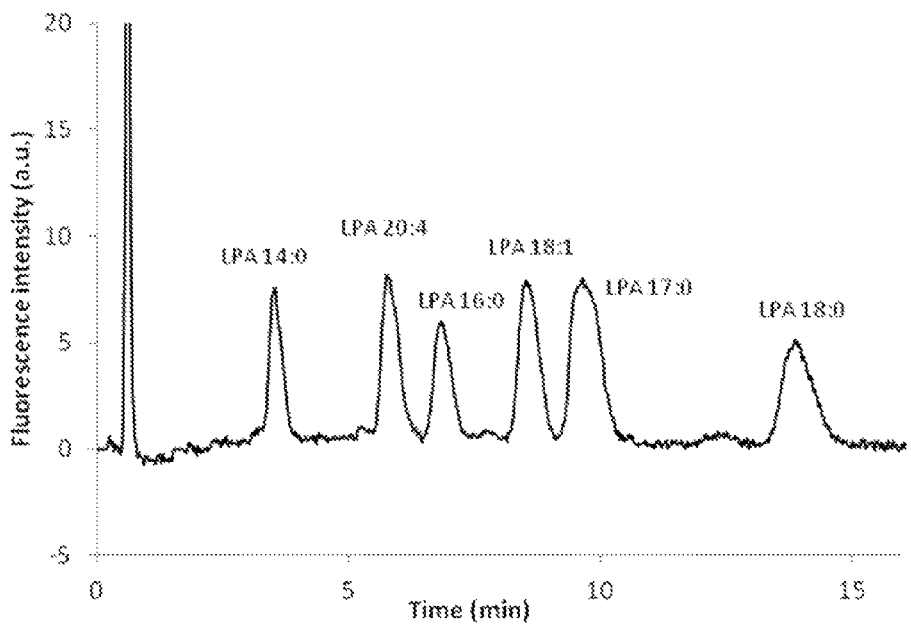
FIG. 4 is an HPLC trace of a LPA mixture (10 µM LPA 14:0, 16:0, 18:0, 18:1, 20:4 and 20 µM LPA 17:0) injected in a 20 µL injection loop. Chromatography conditions: Column: LUNA™ C8 column, 3 µm, 50×2.1 mm, mobile phase: methanol:phosphate buffer (50 mM, pH 2.5) 16:5; flow rate: 0.32 mL/min. Injection volume: 20 µL. Sample concentration: 10 µM in methanol:$H_2O$ 9:1. Post-column reagent: 10 µM DiA in $H_2O$. Reagent flow rate: 0.62 mL/min. Detection wavelength: ex/em 450/570 nm.

FIG. 4 shows a representative trace for the separation and subsequent detection of LPA 14:0, 16:0, 17:0, 18:0, 18:1 and 20:4 with DiA. An LPA mixture (10 μM LPA 14:0, 16:0, 18:0, 18:1, 20:4 and 20 μM LPA 17:0 as an internal standard) was injected in a 20 μL injection loop. Chromatography conditions: (i) column: LUNA™ C8 column, 3 μm, 50×2.1 mm; (ii) mobile phase: MeOH:phosphate buffer (50 mM, pH 2.5) 16:5; (iii) flow rate: 0.32 mL/min.; (iv) injection volume: 20 μL; (v) sample concentration: 10 μM in MeOH:H$_2$O 9:1; (vi) post-column reagent: 10 μM DiA in H$_2$O; (vii) reagent flow rate: 0.62 mL/min; (viii) detection wavelength: ex/em 450/570 nm.

Mixtures of LPAs (in MeOH:H$_2$O 9:1) with concentrations ranging from 0.5-40 μM were evaluated using the same procedure to determine the concentration range over which a linear response was obtained. LPA (17:0), a non-natural LPA, was added to these mixtures at a concentration of 20 μM to act as an internal standard for further quantification. LPA 14:0, LPA 18:0 and LPA 18:1 demonstrated a linear response throughout this range, while LPA 16:0 and LPA 20:4 had a linear response over the range of 0.5-25 μM (FIGS. 5A-5E). Correlation factors ($R^2$) >0.99 were obtained for all of the LPAs (Table 2). The limit of detection (LOD) for each LPA species was determined as the amount of analyte that corresponds to three times the signal of the background noise.

TABLE 2

| LPA species | Retention time (min) | Linear range (μM) | $R^2$ | LOD (μM) |
|---|---|---|---|---|
| 14:0 | 3.50 | 0-40 | 0.9962 | 0.147 |
| 20:4 | 5.56 | 0-25 | 0.9960 | 0.161 |
| 16:0 | 6.64 | 0-25 | 0.9963 | 0.173 |
| 18:1 | 8.35 | 0-40 | 0.9949 | 0.074 |
| 18:0 | 13.75 | 0-40 | 0.9943 | 0.272 |

To make a comparison with the HPLC post-column method, the individual LPA species also were evaluated with LC/ESI/MS/MS. A concentration range of 0-40 μM was selected. LPA (17:0) was also used as an internal standard. FIGS. 6A-E show calibration curves for the individual LPA species evaluated with LC/ESI/MS/MS. Acceptable correlation factors ($R^2$) were obtained for all the LPAs (Table 3). The limit of detection (LOD) for each LPA species was determined as the amount of analyte that corresponds to three times the signal of the background noise

TABLE 3

| LPA species | Retention time (min) | Linear range (μM) | $R^2$ | LOD (μM) |
|---|---|---|---|---|
| 14:0 | 6.30 | 0-40 | 0.9982 | 0.0067 |
| 20:4 | 7.55 | 0-40 | 0.9981 | 0.0099 |
| 16:0 | 8.29 | 0-40 | 0.9986 | 0.0123 |
| 18:1 | 9.10 | 0-40 | 0.9989 | 0.0066 |
| 18:0 | 11.22 | 0-40 | 0.9985 | 0.0156 |

Two blind samples which included some of the LPA subspecies at different concentrations were prepared as above and tested in triplicate using both the HPLC post column method and LC/ESI/MS/MS. The LPA concentrations were in agreement between the two methods and within acceptable error as compared to the theoretical values (Table 4).

TABLE 4

| | Blind A | | | | | Blind B | | | | |
|---|---|---|---|---|---|---|---|---|---|---|
| | Theoretical Value (μM) | HPLC Experimental | | LC/ESI/MS/MS Experimental | | Theoretical Value (μM) | HPLC Experimental | | LC/ESI/MS/MS Experimental | |
| | Concentration | (μM) | % error | (μM) | % error | Concentration | (μM) | % error | (μM) | % error |
| LPA 14:0 | 3.80 | 3.72 | −2.11 | 3.81 | 0.26 | — | — | — | — | — |
| LPA 16:0 | 1.20 | 1.16 | −3.33 | 1.21 | 0.83 | 0.80 | 0.86 | 7.50 | 0.72 | −10.00 |
| LPA 18:0 | 2.50 | 2.34 | −6.40 | 2.62 | 4.80 | 4.20 | 4.26 | 1.43 | 3.83 | −8.81 |

TABLE 4-continued

| | Blind A | | | | | Blind B | | | | |
|---|---|---|---|---|---|---|---|---|---|---|
| | Theoretical Value ($\mu$M) | HPLC Experimental | | LC/ESI/MS/MS Experimental | | Theoretical Value ($\mu$M) | HPLC Experimental | | LC/ESI/MS/MS Experimental | |
| | Concentration | ($\mu$M) | % error | ($\mu$M) | % error | Concentration | ($\mu$M) | % error | ($\mu$M) | % error |
| LPA 18:1 | 0.70 | 0.66 | −5.71 | 0.71 | 1.43 | — | — | — | — | — |
| LPA 20:4 | 4.90 | 4.83 | −1.43 | 5.19 | 5.92 | 2.20 | 2.32 | 5.45 | 2.33 | 5.91 |

Example 3

Quantification of LPAs in Commercial Plasma and Commercial LPA Spiked Plasma

Native LPA concentrations were determined in human plasma from 5 different donors. Plasma Source for Donor A: Lyophilized Human Plasma, Sigma-Aldrich (Catalog # P9523). For donors B, C, D, and E, plasma was collected by Lampire Biological Laboratories Inc., from female donors, processed to obtain platelet-free plasma, and frozen at −80° C. (Catalog #7303809).

The human plasma from these five donors was spiked with 0.5 $\mu$M of each individual LPA. Then, the individual LPA concentrations of these spiked plasma samples were determined. All the samples were analyzed by triplicate using both HPLC-post column and LC/ESI/MS/MS methods.

HPLC-post column conditions: Column—reversed phase C8, 3 $\mu$m, 50×2.0 mm. Mobile phase—methanol:phosphate buffer (pH 2.5)=16:5. Flow rate—0.32 mL/min. Injection volume—20 $\mu$L. Sample concentration—10 $\mu$M in MeOH:H$_2$O 9:1. Post-column reagent—10 $\mu$M DiA in H$_2$O. Reagent flow rate—0.62 mL/min. Detection wavelengths: ex/em 450/570 nm.

LC/ESI/MS/MS conditions: Column LUNA™ C8 column (50×2 mm, 3 $\mu$m) at 40° C. Injection volume—10 $\mu$L.

Mobile phase-MeOH:aqueous formic acid (pH 2.5) 9:1. Flow rate of 0.4 mL/min. Parent and daughter ions were detected in the negative ion mode, sprayer voltage; 3.0 kV, capillary temperature at 300° C.

The LPA concentrations determined by these two methods correlate with each other (Tables 5A-5C). Acceptable standard deviations ($\sigma$) were obtained for each individual LPA for all donors: (a) HPLC-post column method, $\sigma$: 0.002-0.091; (b) LC/ESI/MS/MS method, $\sigma$: 0.002-0.063. The experimental concentration determined for spiked samples is in agreement with the actual spiked concentration. (a) HPLC-post column method: 0.406 to 0.595 $\mu$M. (b) LC/ESI/MS/MS method: 0.370 to 0.592 $\mu$M.

Figure 7:
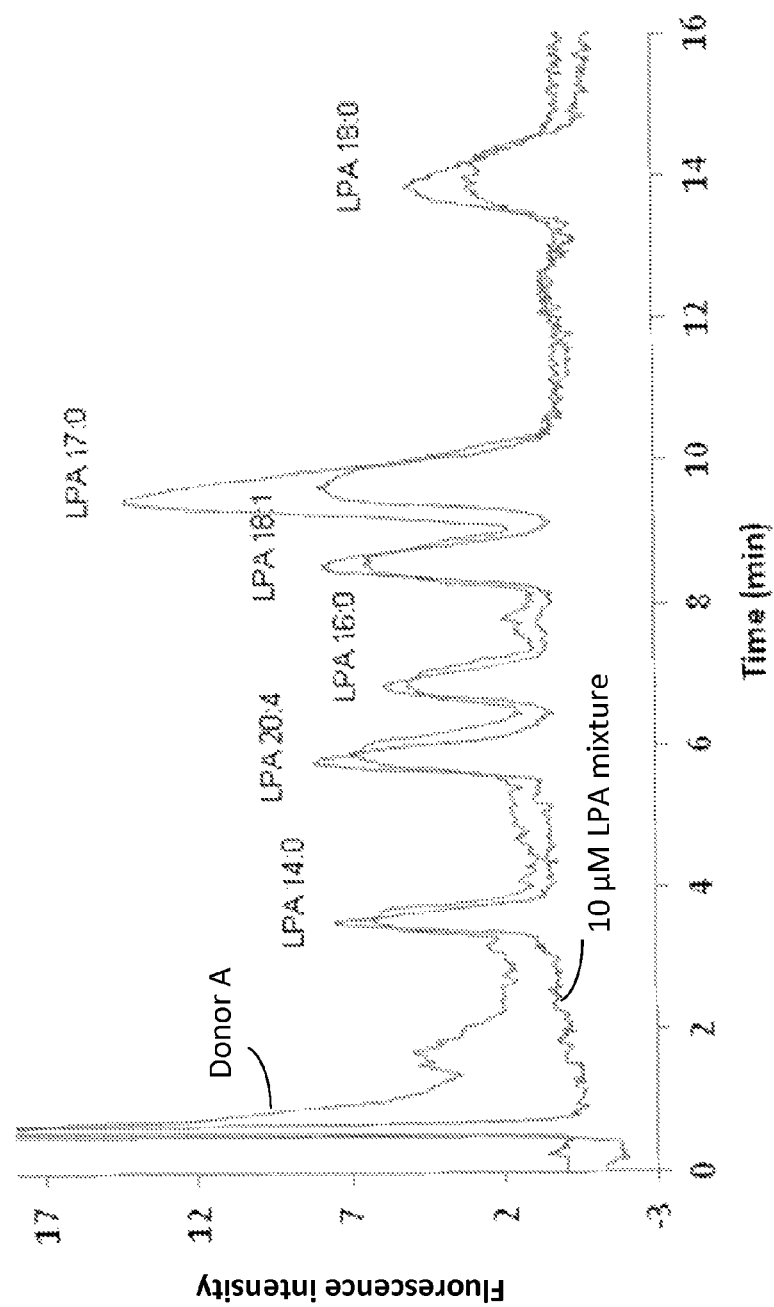
FIG. 7 is an HPLC trace of 10 µM LPAs mixture (LPA 14:0, 16:0, 17:0, 18:0, 18:1 and 20:4) and LPAs isolated from Donor A human plasma. Chromatography conditions: Column—reversed phase C8, 3 µm, 50×2.0 mm; mobile phase—methanol:phosphate buffer (pH 2.5)=16:5; flow rate—0.32 mL/min; injection volume—20 µL; sample concentration—10 µM in MeOH:$H_2O$ 9:1; post-column reagent—10 µM DiA in $H_2O$; reagent flow rate—0.62 mL/min. Detection wavelengths: ex/em 450/570 nm.
Figure 8A:
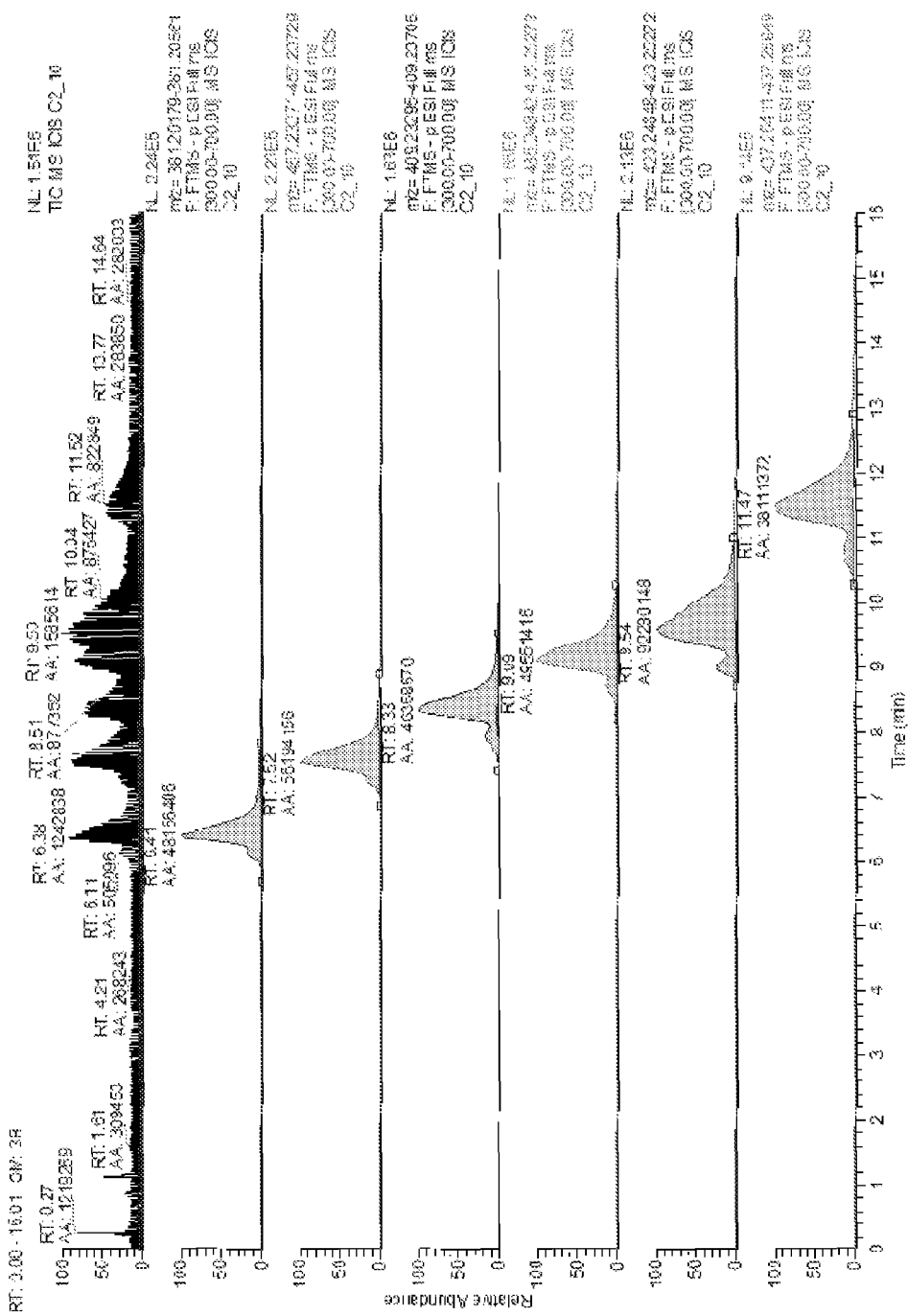
FIGS. 8A and 8B are LC/ESI/MS/MS traces of a 10 µM mixture of standard LPAs (FIG. 8A) and a plasma sample from donor A (FIG. 8B). Column: LUNA™ C8 column (50×2 mm, 3 µm) at 40° C. Injection volume; 10 µL. Mobile phase; MeOH:aqueous formic acid (pH 2.5) 9:1. Flow rate of 0.4 mL/min. Parent and daughter ions were detected in the negative ion mode, sprayer voltage; 3.0 kV, capillary temperature at 300° C.
Figure 8B:
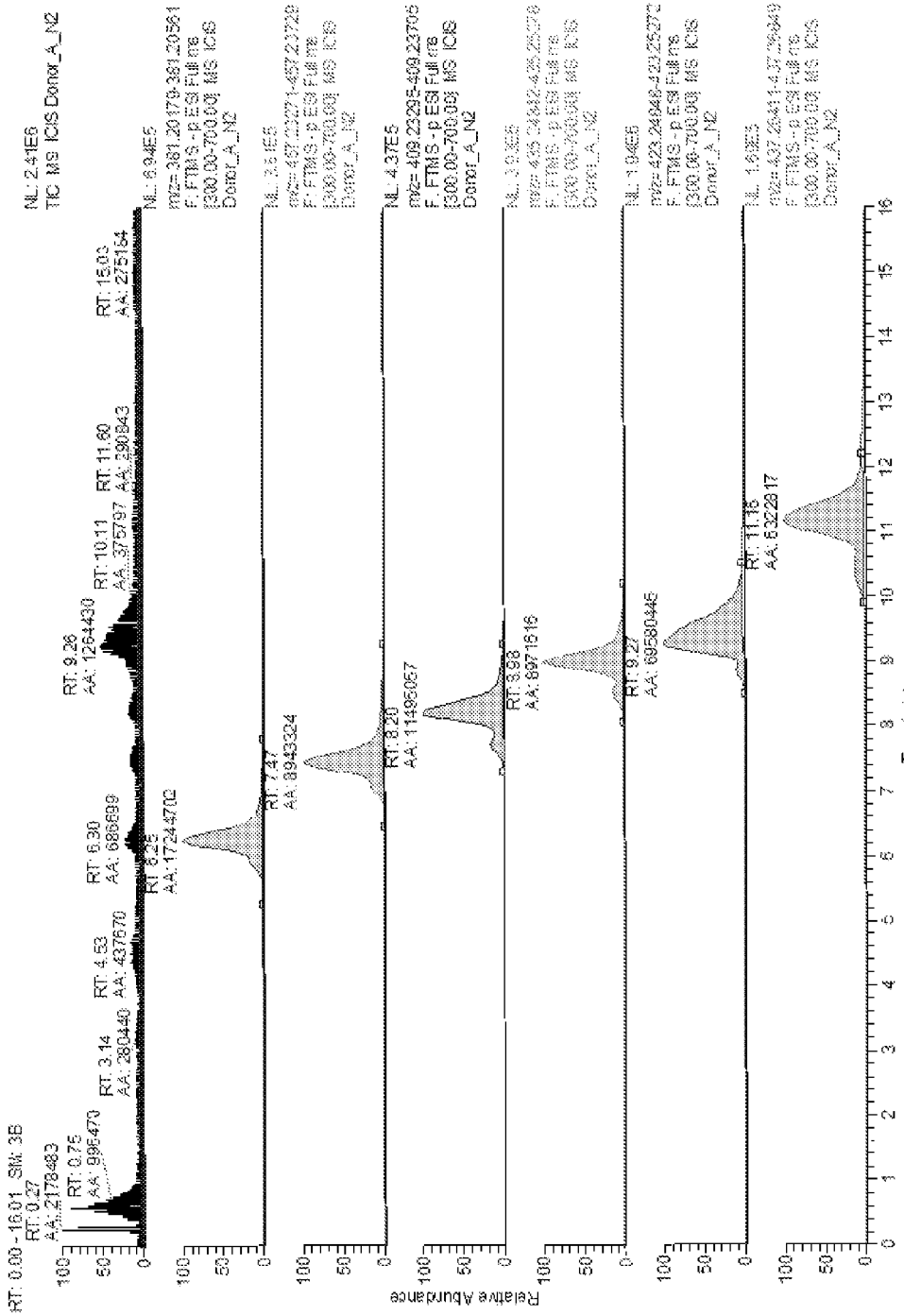

FIG. 7 shows typical traces obtained by the HPLC-post column method for a standard LPA mixture and LPAs isolated from human plasma samples. FIGS. 8A and 8B show typical LC/ESI/MS/MS traces of a 10 $\mu$M mixture of standard LPAs (FIG. 8A) and a plasma sample from donor A (FIG. 8B).

Tables 5A-5C

Summary of Results for LPA Analysis in Human Plasma Using the HPLC Post-Column Fluorescence and LC/ESI/MS/MS Methods

TABLE 5A

| | Non Spiked | | | | | | | | | |
|---|---|---|---|---|---|---|---|---|---|---|
| | Donor A Avg ($\sigma$)* | | Donor B Avg ($\sigma$)* | | Donor C Avg ($\sigma$)* | | Donor D Avg ($\sigma$)* | | Donor E Avg ($\sigma$)* | |
| | HPLC Post-Column | LC/ESI MS/MS | HPLC Post-Column | LC/ESI MS/MS | HPLC Post-Column | LC/ESI MS/MS | HPLC Post-Column | LC/ESI MS/MS | HPLC Post-Column | LC/ESI MS/MS |
| LPA 14:0 | 0.90 (0.01) | 0.92 (0.01) | 0.97 (0.03) | 1.03 (0.01) | 0.76 (0.01) | 0.68 (0.02) | 0.24 (0.00) | 0.23 (0.01) | 0.17 (0.00) | 0.18 (0.01) |
| LPA 20:4 | 0.63 (0.02) | 0.64 (0.03) | 0.98 (0.01) | 0.94 (0.01) | 0.21 (0.02) | 0.27 (0.02) | 0.26 (0.01) | 0.28 (0.01) | 0.20 (0.02) | 0.23 (0.01) |
| LPA 16:0 | 0.76 (0.03) | 0.74 (0.01) | 0.96 (0.02) | 1.04 (0.02) | 0.55 (0.01) | 0.42 (0.04) | 0.45 (0.03) | 0.43 (0.01) | 0.29 (0.00) | 0.28 (0.02) |
| LPA 18:1 | 0.68 (0.01) | 0.65 (0.02) | 1.05 (0.00) | 1.03 (0.02) | 0.37 (0.01) | 0.32 (0.01) | 0.30 (0.02) | 0.38 (0.01) | 0.53 (0.01) | 0.47 (0.02) |
| LPA 18:0 | 0.56 (0.02) | 0.60 (0.01) | 0.99 (0.01) | 0.93 (0.01) | 0.29 (0.03) | 0.23 (0.01) | 0.33 (0.02) | 0.31 (0.00) | 0.33 (0.00) | 0.30 (0.01) |
| Total LPA | 3.53 (0.03) | 3.56 (0.02) | 4.96 (0.04) | 4.97 (0.04) | 2.18 (0.02) | 1.91 (0.09) | 1.57 (0.03) | 1.63 (0.03) | 1.52 (0.02) | 1.45 (0.05) |

TABLE 5B

| | Donor A Avg (σ)* | | Donor B Avg (σ)* | | Donor C Avg (σ)* | | Donor D Avg (σ)* | | Donor E Avg (σ)* | |
|---|---|---|---|---|---|---|---|---|---|---|
| | HPLC Post-Column | LC/ESI MS/MS | HPLC Post-Column | LC/ESI MS/MS | HPLC Post-Column | LC/ESI MS/MS | HPLC Post-Column | LC/ESI MS/MS | HPLC Post-Column | LC/ESI MS/MS |
| LPA 14:0 | 1.31 (0.09) | 1.33 (0.05) | 1.43 (0.975) | 1.45 (0.03) | 1.25 (0.02) | 1.21 (0.04) | 0.65 (0.02) | 0.68 (0.02) | 0.61 (0.02) | 0.60 (0.00) |
| LPA 20:4 | 1.09 (0.05) | 1.06 (0.03) | 1.41 (0.976) | 1.43 (0.01) | 0.64 (0.01) | 0.67 (0.05) | 0.67 (0.01) | 0.65 (0.04) | 0.75 (0.01) | 0.77 (0.01) |
| LPA 16:0 | 1.19 (0.09) | 1.19 (0.01) | 1.45 (1.015) | 1.60 (0.03) | 1.05 (0.05) | 0.97 (0.04) | 0.88 (0.02) | 0.83 (0.04) | 0.71 (0.00) | 0.76 (0.01) |
| LPA 18:1 | 1.18 (0.01) | 1.10 (0.03) | 1.47 (1.021) | 1.55 (0.02) | 0.96 (0.05) | 0.79 (0.06) | 0.87 (0.02) | 0.85 (0.03) | 0.97 (0.02) | 1.03 (0.00) |
| LPA 18:0 | 1.06 (0.03) | 1.05 (0.01) | 1.56 (1.097) | 1.47 (0.01) | 0.79 (0.01) | 0.79 (0.02) | 0.85 (0.02) | 0.82 (0.01) | 0.84 (0.01) | 0.89 (0.00) |
| Total LPA | 5.83 (0.22) | 5.73 (0.11) | 7.33 (5.102) | 7.50 (0.08) | 4.69 (0.08) | 4.44 (0.12) | 3.91 (0.03) | 3.83 (0.12) | 3.88 (0.04) | 4.06 (0.01) |

TABLE 5C

Difference between spiked and non-spiked

| | Donor A Exp Avg/ Spiked LPA conc) | | Donor B Exp Avg/ Spiked LPA conc) | | Donor C Exp Avg/ Spiked LPA conc) | | Donor D Exp Avg/ Spiked LPA conc) | | Donor E Exp Avg/ Spiked LPA conc) | |
|---|---|---|---|---|---|---|---|---|---|---|
| | HPLC Post-Column | LC/ESI MS/MS | HPLC Post-Column | LC/ESI MS/MS | HPLC Post-Column | LC/ESI MS/MS | HPLC Post-Column | LC/ESI MS/MS | HPLC Post-Column | LC/ESI MS/MS |
| LPA 14:0 | 0.41/ 0.50 | 0.41/ 0.50 | 0.47/ 0.50 | 0.41/ 0.50 | 0.49/ 0.50 | 0.53/ 0.50 | 0.41/ 0.50 | 0.46/ 0.50 | 0.43/ 0.50 | 0.42/ 0.50 |
| LPA 20:4 | 0.47/ 0.50 | 0.42/ 0.50 | 0.43/ 0.50 | 0.50/ 0.50 | 0.42/ 0.50 | 0.40/ 0.50 | 0.41/ 0.50 | 0.37/ 0.50 | 0.55/ 0.50 | 0.55/ 0.50 |
| LPA 16:0 | 0.43/ 0.50 | 0.45/ 0.50 | 0.49/ 0.50 | 0.56/ 0.50 | 0.50/ 0.50 | 0.56/ 0.50 | 0.44/ 0.50 | 0.40/ 0.50 | 0.42/ 0.50 | 0.48/ 0.50 |
| LPA 18:1 | 0.49/ 0.50 | 0.45/ 0.50 | 0.42/ 0.50 | 0.51/ 0.50 | 0.60/ 0.50 | 0.48/ 0.50 | 0.57/ 0.50 | 0.47/ 0.50 | 0.45/ 0.50 | 0.56/ 0.50 |
| LPA 18:0 | 0.50/ 0.50 | 0.44/ 0.50 | 0.57/ 0.50 | 0.55/ 0.50 | 0.51/ 0.50 | 0.56/ 0.50 | 0.52/ 0.50 | 0.51/ 0.50 | 0.51/ 0.50 | 0.59/ 0.50 |
| Total LPA | 2.31/ 2.50 | 2.17/ 2.50 | 2.37/ 2.50 | 2.53/ 2.50 | 2.52/ 2.50 | 2.53/ 2.50 | 2.35/ 2.50 | 2.20/ 2.50 | 2.36/ 2.50 | 2.60/ 2.50 |

*Avg.: n = 3
σ = standard deviation

Example 4

GRBI Synthesis

The synthetic route for GRBI (1-(3',6'-bis(diethylamino)-3-oxospiro[isoindoline-1,9'-xanthene]-2-yl)guanidine) is described in Scheme 1. Compound 1 can be synthesized in 4 steps; starting from the commercially available Rhodamine B. Compound 4 was obtained as described with a yield of 95%. The reaction of 4 with 1,3-bis-Boc-2-methyl-2-thiopseudourea and HgCl$_2$ produced Boc-protected compound 5 in 90% yield. Guanidine deprotection was accomplished with TFA in DCM, which upon neutralization under basic condition gave compound 1 in 60% yield.

Scheme 1

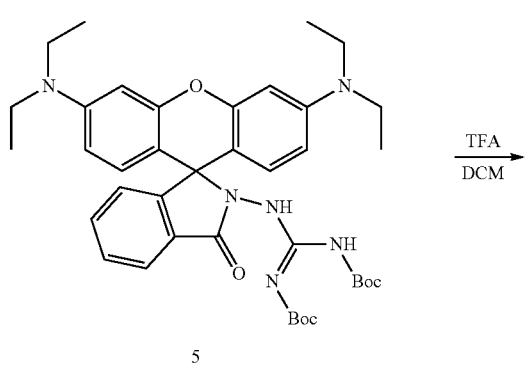

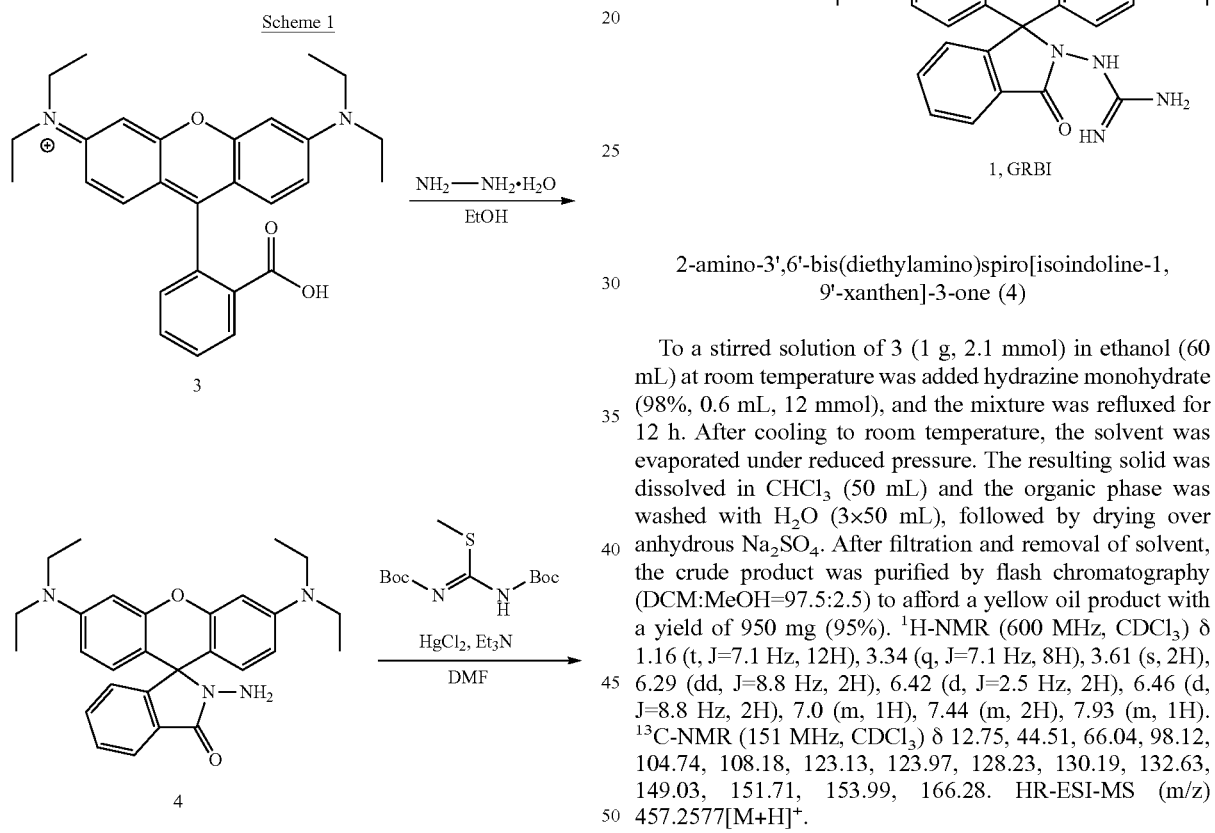

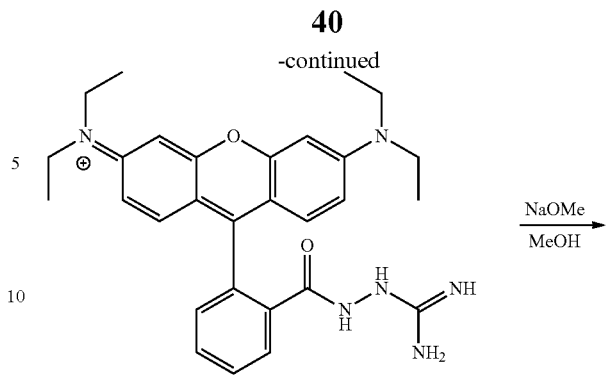

2-amino-3',6'-bis(diethylamino)spiro[isoindoline-1, 9'-xanthen]-3-one (4)

To a stirred solution of 3 (1 g, 2.1 mmol) in ethanol (60 mL) at room temperature was added hydrazine monohydrate (98%, 0.6 mL, 12 mmol), and the mixture was refluxed for 12 h. After cooling to room temperature, the solvent was evaporated under reduced pressure. The resulting solid was dissolved in CHCl$_3$ (50 mL) and the organic phase was washed with H$_2$O (3×50 mL), followed by drying over anhydrous Na$_2$SO$_4$. After filtration and removal of solvent, the crude product was purified by flash chromatography (DCM:MeOH=97.5:2.5) to afford a yellow oil product with a yield of 950 mg (95%). $^1$H-NMR (600 MHz, CDCl$_3$) δ 1.16 (t, J=7.1 Hz, 12H), 3.34 (q, J=7.1 Hz, 8H), 3.61 (s, 2H), 6.29 (dd, J=8.8 Hz, 2H), 6.42 (d, J=2.5 Hz, 2H), 6.46 (d, J=8.8 Hz, 2H), 7.0 (m, 1H), 7.44 (m, 2H), 7.93 (m, 1H). $^{13}$C-NMR (151 MHz, CDCl$_3$) δ 12.75, 44.51, 66.04, 98.12, 104.74, 108.18, 123.13, 123.97, 128.23, 130.19, 132.63, 149.03, 151.71, 153.99, 166.28. HR-ESI-MS (m/z) 457.2577[M+H]$^+$.

(E)-tert-butyl(3',6'-bis(diethylamino)-3-oxospiro[isoindoline-1,9'-xanthene]-2-ylamino)(tert-butoxycarbonylamino)methylenecarbamate (5)

To a stirred solution of 4 (290 mg, 0.64 mmol), HgCl$_2$ (190 mg, 0.70 mmol) and 1,3-bis-Boc-2-methyl-2-thiopseudourea (188 mg, 0.70 mmol) in anhydrous DMF (10 mL) under argon was added triethylamine (0.45 mL, 3.18 mmol). The resulting suspension was stirred in an ice bath for 2 h, and then at room temperature for 12 h. The mixture was diluted with CHCl$_3$ and filtered through a short Celite column. The filtrate was washed with saturated NaHCO$_3$ solution (25 mL) and H$_2$O (3×25 mL). The combined organic phase was dried over anhydrous Na$_2$SO$_4$. After filtration and removal of solvent, the crude product was purified by flash chromatography (EtOAc:hexane=1:2) to afford a purple solid with a yield of 410 mg (90%). $^1$H-NMR (600 MHz, CDCl$_3$) δ 1.16 (t, J=6.9 Hz, 12H), 1.37 (s, J=9.2 Hz, 9H), 1.38 (s, J=20.5 Hz, 9H), 3.33 (m, J=6.8 Hz, 8H), 6.27 (dd, J=32.5, 8.2 Hz, 2H), 6.36 (d, J=14.9 Hz, 2H), 6.77 (s, 1H), 7.10 (t, J=7.3 Hz, 1H), 7.46 (m, 2H), 7.94 (t, J=10.8 Hz, 1H), 9.33 (s, 1H), 11.16 (s, 1H). $^{13}$C NMR (151 MHz, CDCl$_3$) δ 12.78, 28.07, 28.35, 44.47, 66.68, 78.80, 83.25, 97.81, 104.55, 108.02, 123.60, 124.19, 128.02, 128.23, 129.03, 133.21, 149.03, 152.35, 153.75, 156.39, 163.56. HR-ESI-MS (m/z) 699.3932 [M+H]$^+$.

N-(9-(2-(2-carbamimidoylhydrazinecarbonyl)phenyl)-6-(diethylamino)-3H-xanthen-3-ylidene)-N-ethyl-ethanaminium 2,2,2-trifluoroacetate (6)

To a stirred solution of 5 (380 mg, 0.55 mmol) in CH$_2$Cl$_2$ (2 mL) was added slowly a solution of trifluoroacetic acid (2 mL) in CH$_2$Cl$_2$ (2 mL). Stirring at room temperature was continued until the reaction was adjudged complete by TLC analysis. Solvent and excess trifluoroacetic acid were evaporated under reduced pressure to afford the trifluoroacetate salt as a dark purple solid for the next reaction without further purification.

1-(3',6'-bis(diethylamino)-3-oxospiro[isoindoline-1, 9'-xanthene]-2-yl)guanidine (1)

To a stirred solution of 6 in anhydrous MeOH (3 mL), 0.5 M NaOMe solution (3 mL) was added, and the mixture was stirred at room temperature for 1 h. The solvent was evaporated under reduced pressure, and the resulting solid was dissolved in CHCl$_3$ (50 mL). The organic phase was washed with NaHCO$_3$ solution (25 mL) and H$_2$O (3×25 mL). The combined organic phase was dried over anhydrous Na$_2$SO$_4$. After filtration and removal of solvent, the crude product was purified by flash chromatography (DCM:MeOH=9:1) to afford a purple solid with a yield of 160 mg (60%). $^1$H-NMR (600 MHz, DMSO) δ 1.08 (t, J=7.0 Hz, 3H), 3.30 (q, J=7.1 Hz, 8H), 5.51 (d, J=293.9 Hz, 4H), 6.27 (dd, J=8.9, 2.5 Hz, 2H), 6.30 (d, J=2.5 Hz, 2H), 6.56 (d, J=7.3 Hz, 2H), 6.88 (d, J=6.9 Hz, 1H), 7.42 (m, 2H), 7.71 (d, J=6.5 Hz, 1H). $^{13}$C-NMR (151 MHz, DMSO) δ 12.49, 43.63, 65.29, 97.15, 105.99, 107.39, 121.78, 123.17, 127.77, 128.72, 130.55, 131.59, 147.93, 152.34, 152.78, 158.53. HR-ESI-MS (m/z) 499.2827[M+H]$^+$.

Example 5

GRBII Synthesis

The synthetic route for GRBII (3',6'-bis(diethylamino)-3-oxospiro[isoindoline-1,9'-xanthene]-2-carboximidamide) is described in Scheme 2. Compound 2 can be synthesized in 4 steps; starting from the commercially available Rhodamine B Base. Compound 8 was obtained according to the procedure described below. Without further purification, the reaction of 8 with 1,3-Bis(tert-butoxycarbonyl)guanidine and K$_2$CO$_3$ produced Boc-protected compound 9 in 62% yield. Guanidine deprotection was accomplished with TFA in DCM, which upon neutralization under basic conditions gave compound 2 in 52% yield.

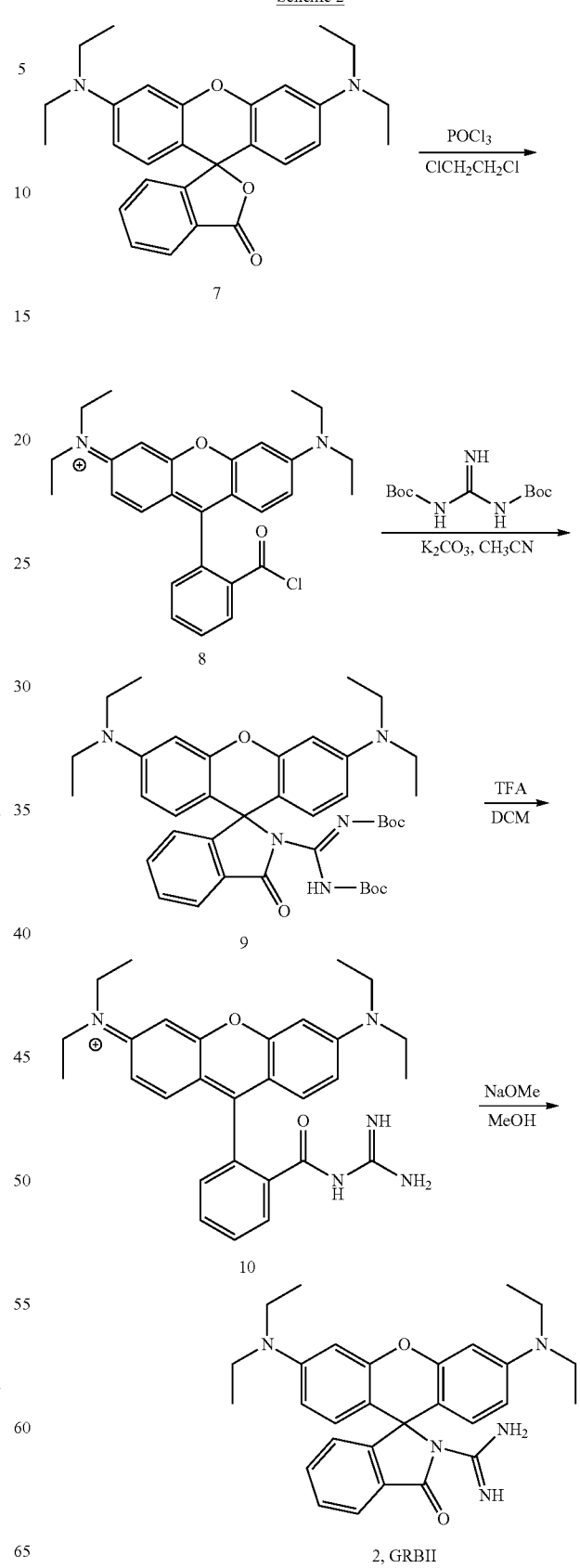

Scheme 2

N-(9-(2-(chlorocarbonyl)phenyl)-6-(diethylamino)-3H-xanthen-3-ylidene)-N-ethylethanaminium(8)

To a solution of 7 (500 mg, 1.13 mmol) in anhydrous 1,2-dichloroethane (5 mL), was added a solution of phosphorus oxychloride (0.26 mL, 2.8 mmol) in 1,2-dichloroethane (5 mL) drop wise over 5 min, the mixture was refluxed for 4 h. After the reaction mixture was cooled to room temperature, the solvent was evaporated under reduced pressure to yield rhodamine B acyl chloride without further purification.

E)-tert-butyl (3',6'-bis(diethylamino)-3-oxospiro[isoindoline-1,9'-xanthene]-2-yl)methanediylidenedicarbamate (9)

1,3-Bis(tert-butoxycarbonyl)guanidine (290 mg, 1.13 mmol) and $K_2CO_3$ (0.62 g, 4.5 mmol) were dissolved in anhydrous acetonitrile (5 mL) under argon. The crude rhodamine B acyl chloride was dissolved in anhydrous acetonitrile (5 mL) and added drop wise to the solution over 3 h. After 12 h, the solvent was evaporated under reduced pressure; the residue was dissolved in chloroform and washed with saturated $NaHCO_3$ solution (25 mL) and $H_2O$ (3×25 mL), the organic phase was dried over anhydrous $Na_2SO_4$. After filtration and removal of solvent, the crude product was purified by flash chromatography (EtOAc: Hexane=1:2) to afford a yellow solid with a yield of 476 mg (62%). $^1$H-NMR (600 MHz, $CDCl_3$) δ 1.13 (t, J=7.1 Hz, 12H), 1.35 (s, 9H), 1.41 (s, 9H), 3.30 (m, 8H), 6.18 (dd, J=8.8, 2.6 Hz, 2H), 6.30 (d, J=8.8 Hz, 2H), 6.35 (d, J=2.6 Hz, 2H), 7.16 (d, J=7.7 Hz, 1H), 7.51 (m, 1H), 7.58 (td, J=7.5, 1.1 Hz, 1H), 7.94 (d, J=7.6 Hz, 1H), 10.75 (s, 1H). $^{13}$C-NMR (151 MHz, $CDCl_3$) δ 12.78, 28.15, 28.18, 44.40, 68.30, 78.74, 81.78, 97.72, 106.68, 107.23, 123.59, 125.09, 127.65, 128.75, 129.20, 135.16, 139.08, 148.97, 150.16, 153.42, 154.20, 156.14, 171.05. HR-ESI-MS (m/z) 684.3794 $[M+H]^+$.

N-(9-(2-(carbamimidoylcarbamoyl)phenyl)-6-(diethylamino)-3H-xanthen-3-ylidene)-N-ethylethanaminium 2,2,2-trifluoroacetate (10)

To a stirred solution of 9 (300 mg, 0.44 mmol) in $CH_2Cl_2$ (2 mL) was added slowly a solution of trifluoroacetic acid (2 mL) in $CH_2Cl_2$ (2 mL). Stirring at room temperature continued until the reaction was determined to be complete by TLC analysis. Solvent and excess of trifluoroacetic acid was evaporated under reduced pressure to afford the trifluoroacetate salt as a dark purple solid for next reaction without further purification.

3',6'-bis(diethylamino)-3-oxospiro[isoindoline-1,9'-xanthene]-2-carboximidamide (2)

To a stirred solution of 10 in anhydrous MeOH (3 mL), 0.5 M NaOMe solution (3 mL) was added and the mixture was stirred at room temperature for 1 h. The solvent was evaporated under reduced pressure and the resulting solid was dissolved in $CHCl_3$ (50 mL) and the organic phase was washed with $NaHCO_3$ solution (25 mL) and $H_2O$ (3×25 mL), the combined organic phase was dried over anhydrous $Na_2SO_4$. After filtration and removal of solvent, the crude product was purified by flash chromatography (DCM: MeOH=9:1) to afford a purple solid with a yield of 110 mg (52%). $^1$H-NMR (600 MHz, DMSO) δ 1.09 (t, J=7.0 Hz, 12H), 3.34 (q, J=7.1 Hz, 8H), 6.42 (dd, J=9.0, 2.6 Hz, 2H), 6.45 (d, J=2.5 Hz, 2H), 6.72 (d, J=8.9 Hz, 2H), 7.01 (d, J=7.8 Hz, 1H), 7.58 (m, 1H), 7.68 (m, J=1.1 Hz, 1H), 7.69 (bs, 3H), 7.99 (d, J=7.7 Hz, 1H). $^{13}$C-NMR (151 MHz, DMSO) δ 12.38, 43.69, 79.18, 97.67, 103.08, 108.69, 123.65, 124.39, 124.53, 127.22, 129.43, 136.51, 149.17, 151.72, 153.52, 153.64, 169.01. HR-ESI-MS (m/z) 484.2751 $[M+H]^+$.

Example 6

LPA Universal Detection with GRBI and GRBII

The spiro guanidine rhodamines GRBI and GRBII were evaluated as universal fluorophores for the detection and quantification of lysophosphatidic acid (LPA).

LPA14:0, 16:0, 18:0, 18:1 were obtained by protonation of their corresponding sodium salt respectively. 100 mg of LPA sodium salt were dissolved in 15 mL of a solvent mixture $CHCl_3$:MeOH (2:1), followed by the addition of 2 mL DI water. After shaking the solution, the phases were allowed to separate, and the pH of the aqueous phase was adjusted with 3 M HCl to pH 2.5-3.0. The organic phase was separated, and the solvent removed under reduced pressure.

Figure 9:
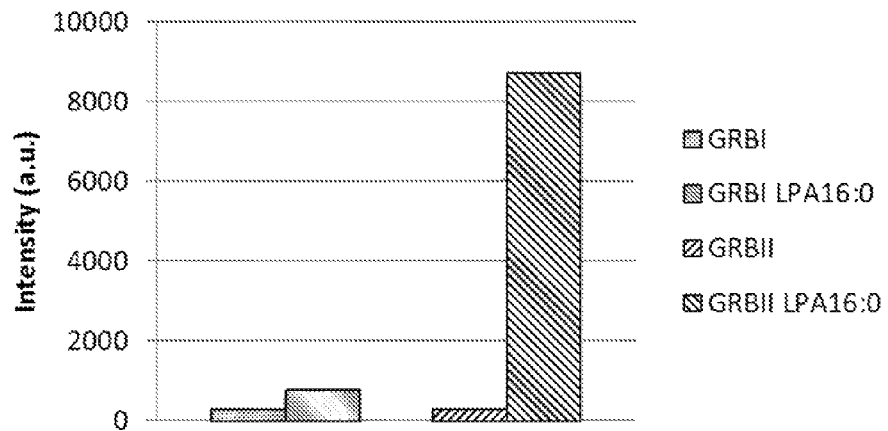
FIG. 9 is a bar graph illustrating the relative fluorescence emission obtained from two embodiments of the disclosed probes (GRBI and GRBII) when combined with LPA 16:0; Ex/Em=550 nm/570 nm, final probe concentration 5 µM, final LPA16:0 concentration 10 µM, solvent system DMSO 2.5% in chloroform.

The fluorescence emission intensity of GRBI and GRBII in the presence of 10 μM LPA16:0 in 2.5% DMSO/chloroform was evaluated. The final probe concentration was 5 μM. An excitation wavelength of 550 nm was used, and fluorescence emission at 570 nm was measured. As shown in FIG. 9, GRBII exhibited greater fluorescence emission in the presence of LPA 16:0 as compared to GRBI.

Figure 10:
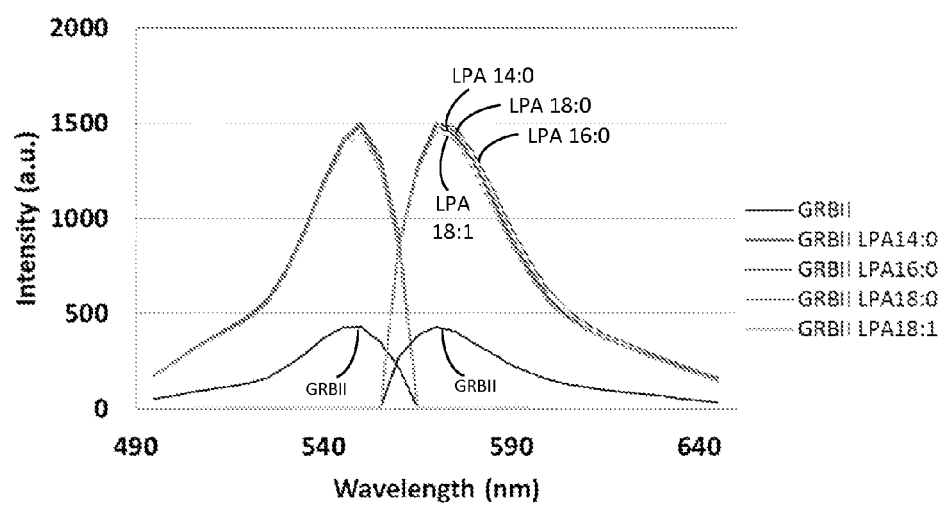
FIG. 10 shows fluorescence spectra of GRBII alone and GRBII in the presence of LPA14:0, 16:0, 18:0, 18:1, ex/em=550 nm/570 nm, final probe concentration 5 µM, final LPA concentration 10 µM, solvent system $CHCl_3$:DMSO 9:1.

Based on these results; the performance of the GRBII fluorophore for LPA detection was further explored. From the evaluation of a series of solvent systems, as well as LPA sample preparation experiments, it was found that GRBII gave the same fluorescence enhancement in the presence of the individual LPAs (LPA14:0, LPA16:0, LPA18:0 and LPA18:1) included in this study. A DMSO titration in chloroform showed that a $CHCl_3$: DMSO 9:1 mixture gave the best results (FIG. 10). In each case, the LPA concentration was 10 μM, and the final GRBII concentration was 5 μM. As seen in FIG. 9, GRBII produced the same fluorescence intensity with each of the LPAs, demonstrating that GRBII can be used as a universal LPA detection agent.

Figure 11:
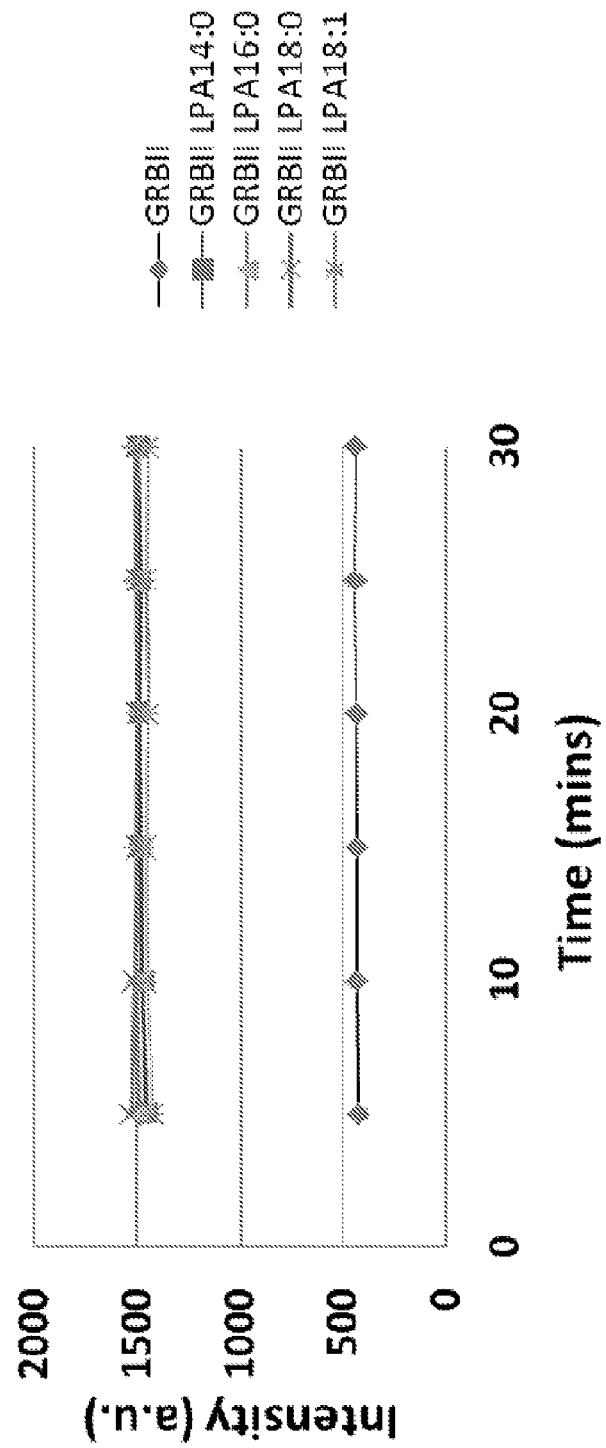
FIG. 11 is a graph of fluorescence intensity of GRBII alone and in the presence of LPA14:0, 16:0, 18:0, 18:1 over time, ex/em=550 nm/570 nm, final probe concentration 5 µM, final LPA concentration 10 µM, solvent system $CHCl_3$:DMSO 9:1.

The fluorescence stability was monitored over time. As shown in FIG. 11, fluorescence intensity remained substantially constant over 30 minutes.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound according to
(a) general formula I

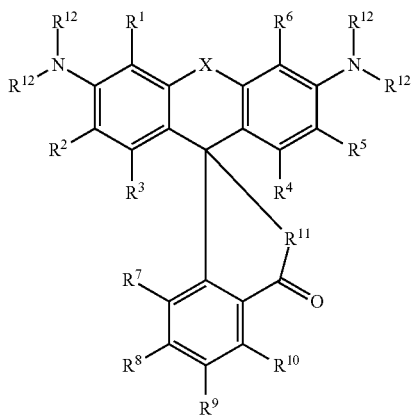

wherein:
- $R^1$-$R^6$ independently are hydrogen, hydroxyl, thiol, $C_1$-$C_{10}$ alkyl, carboxyalkyl, amino, $C_1$-$C_{10}$ alkoxy, or halogen,
- $R^7$-$R^{10}$ independently are hydrogen, alkyl, acyl, carboxyl, nitro, amino, alkylamino, or —$SO_3H$,
- $R^{11}$ is N—C(=$R^{13}$)—$NH_2$, N—C($NH_2$)=N—C(=$R^{13}$)—$NH_2$, or N—NH—C($NH_2$)=N—C(=$R^{13}$)—$NH_2$, where $R^{13}$ is O, S, or NH, or $R^{11}$ is N—NH—C(=$R^{13}$)—$NH_2$, where $R^{13}$ is O or NH,
- each $R^{12}$ independently is hydrogen or lower alkyl, or each of $R^1$, $R^2$, $R^5$, and $R^6$ may together with an adjacent $R^{12}$ and N atom form a 6-membered heterocyclic ring, and
- X is O, S, $CH_2$, NH, or $SiR^{14}$ where $R^{14}$ is H or $C_1$-$C_{10}$ alkyl; or (b) general formula II

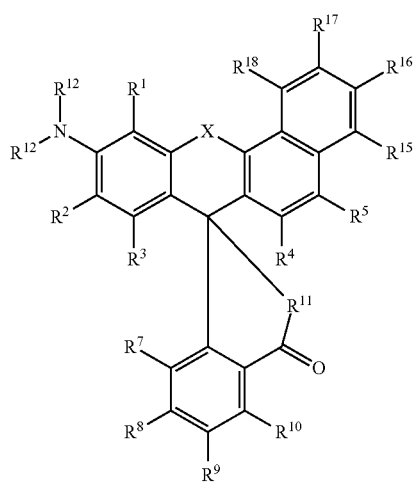

wherein:
- $R^1$-$R^5$, $R^{15}$, $R^{17}$, and $R^{18}$ independently are hydrogen, hydroxyl, thiol, $C_1$-$C_{10}$ alkyl, carboxyalkyl, amino, $C_1$-$C_{10}$ alkoxy, or halogen,
- $R^{16}$ is —$N(R^{12})_2$,
- $R^7$-$R^{10}$ independently are hydrogen, alkyl, acyl, carboxyl, nitro, amino, alkylamino, or —$SO_3H$,
- $R^{11}$ is N—C(=$R^{13}$)—$NH_2$, N—NH—C(=$R^{13}$)—$NH_2$, N—C($NH_2$)=N—C(=$R^{13}$)—$NH_2$, or N—NH—C($NH_2$)=N—C(=$R^{13}$)—$NH_2$, where $R^{13}$ is O, S, or NH,
- each $R^{12}$ independently is hydrogen or $C_1$-$C_{10}$ alkyl, or each of $R^1$, $R^2$, $R^{15}$, and $R^{17}$ may together with an adjacent $R^{12}$ and N atom form a 6-membered heterocyclic ring, and
- X is O, S, $CH_2$, NH, or $SiR^{14}$ where $R^{14}$ is H or $C_1$-$C_{10}$ alkyl; or (c) general formula III

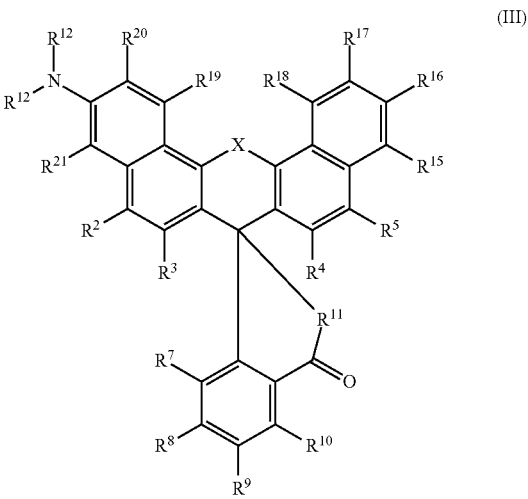

wherein:
- $R^2$-$R^5$, $R^{15}$, $R^{17}$, and $R^{19}$-$R^{21}$ independently are hydrogen, hydroxyl, thiol, $C_1$-$C_{10}$ alkyl, carboxyalkyl, amino, $C_1$-$C_{10}$ alkoxy, or halogen,
- one of $R^{16}$ and $R^{18}$ is hydrogen, hydroxyl, thiol, lower alkyl, carboxyalkyl, amino, $C_1$-$C_{10}$ alkoxy, or halogen, and the other of $R^{16}$ and $R^{18}$ is —$N(R^{12})_2$,
- $R^7$-$R^{10}$ independently are hydrogen, alkyl, acyl, carboxyl, nitro, amino, alkylamino, or —$SO_3H$,
- $R^{11}$ is N—C(=$R^{13}$)—$NH_2$, N—NH—C(=$R^{13}$)—$NH_2$, N—C($NH_2$)=N—C(=$R^{13}$)—$NH_2$, or N—NH—C($NH_2$)=N—C(=$R^{13}$)—$NH_2$, where $R^{13}$ is O, S, or NH,
- each $R^{12}$ independently is hydrogen or $C_1$-$C_{10}$ alkyl, or if $R^{16}$ is —$N(R^{12})_2$, each of $R^{15}$, $R^{17}$, $R^{20}$, and $R^{21}$ may together with an adjacent $R^{12}$ and N form a 6-membered heterocyclic ring, and X is O, S, CH$_2$, NH, or SiR$^{14}$ where R$^{14}$ is H or C$_1$-C$_{10}$ alkyl; or (d) general formula IV

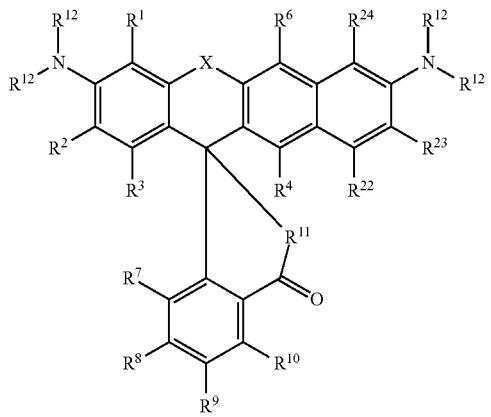

wherein:
R$^1$-R$^4$, R$^6$, and R$^{22}$-R$^{24}$ independently are hydrogen, hydroxyl, thiol, C$_1$-C$_{10}$ alkyl, carboxyalkyl, amino, C$_1$-C$_{10}$ alkoxy, or halogen, R$^7$-R$^{10}$ independently are hydrogen, alkyl, acyl, carboxyl, nitro, amino, alkylamino, or —SO$_3$H, R$^{11}$ is N—C(=R$^{13}$)—NH$_2$, N—NH—C(=R$^{13}$)—NH$_2$, N—C(NH$_2$)=N—C(=R$^{13}$)—NH$_2$, or N—NH—C(NH$_2$)=N—C(=R$^{13}$)—NH$_2$, where R$^{13}$ is O, S, or NH, each R$^{12}$ independently is hydrogen or C$_1$-C$_{10}$ alkyl, or each of R$^1$, R$^2$, R$^{23}$, and R$^{24}$ may together with an adjacent R$^{12}$ and N form a 6-membered heterocyclic ring, and X is O, S, CH$_2$, NH, or SiR$^{14}$ where R$^{14}$ is H or C$_1$-C$_{10}$ alkyl.

2. The compound of claim 1, wherein X is O.

3. The compound of claim 1 according to:
general formula I, wherein R$^1$-R$^{10}$ are H;
general formula II, wherein R$^1$-R$^5$; R$^7$-R$^{10}$, R$^{15}$, R$^{17}$, and R$^{18}$ are hydrogen;
general formula III, wherein R$^2$-R$^5$; R$^7$-R$^{10}$, R$^{15}$, R$^{17}$, and R$^{19}$-R$^{21}$ are hydrogen, one of R$^{16}$ and R$^{18}$ is hydrogen, and the other of R$^{16}$ and R$^{18}$ is —N(R$^{12}$)$_2$; or
general formula IV, wherein R$^1$-R$^4$, R$^{6-10}$, and R$^{22}$-R$^{24}$ are hydrogen.

4. The compound of claim 1, wherein the compound is

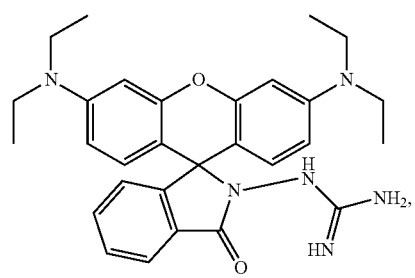

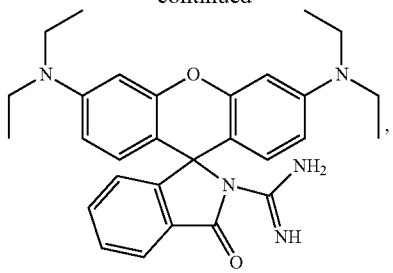

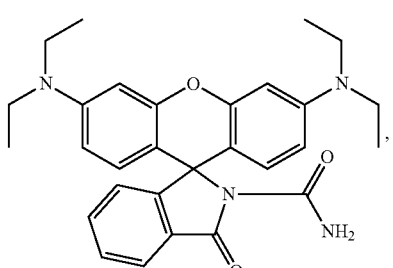

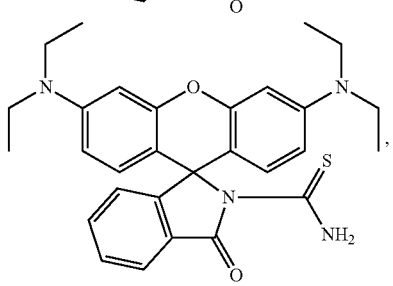

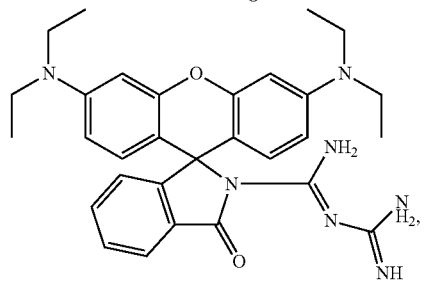

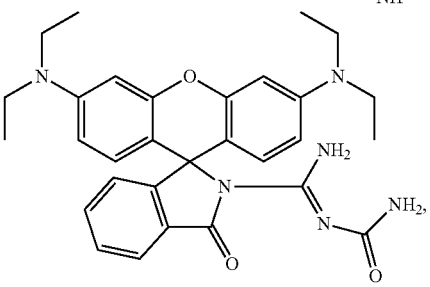

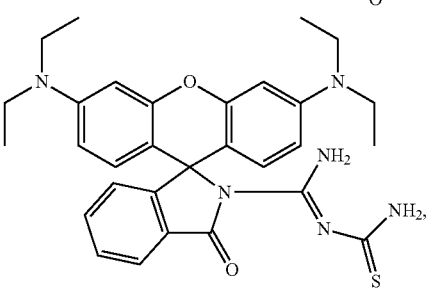

-continued

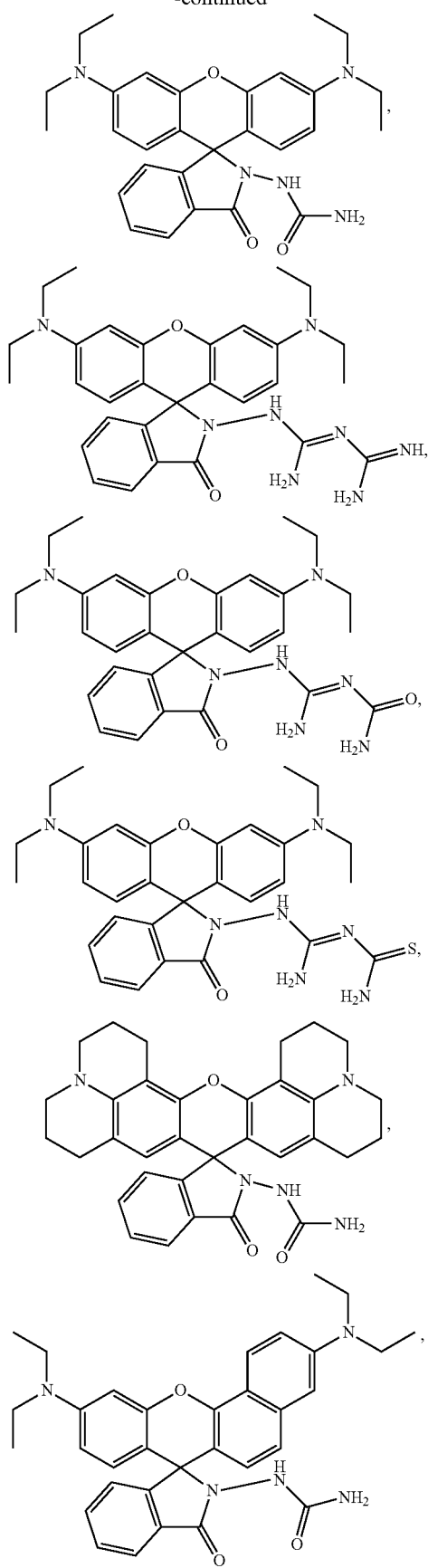

-continued

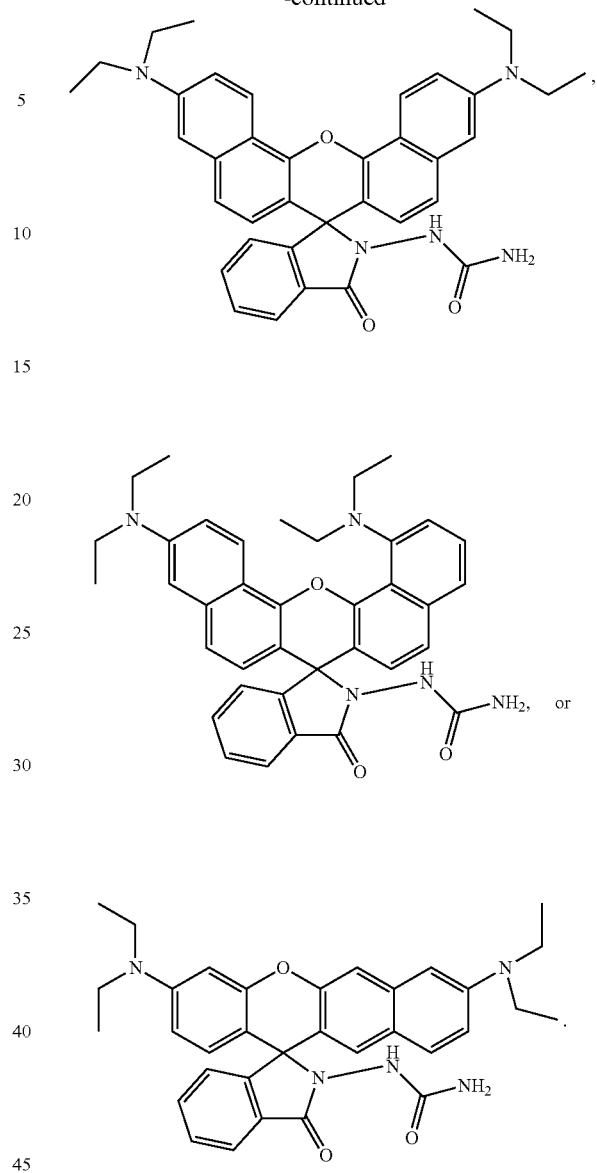

5. A method for quantifying lysophosphatidic acid species, comprising:
combining a sample that may include one or more lysophosphatidic acid species with a compound according to claim 1 in a solvent comprising dimethylsulfoxide in methanol to form a solution;
exposing the solution to a light source;
measuring fluorescence intensity of the solution; and
determining, based on the fluorescence intensity, a total concentration of lysophatidic acid species in the sample.

6. The method of claim 5, further comprising obtaining the sample by extracting lysophosphatidic acid species from a sample comprising plasma or serum, wherein the sample comprising plasma or serum is obtained from a subject suspected of being at risk of a condition associated with an aberrant LPA level, the method further comprising determining a risk level for the condition, wherein the risk level is based at least in part on the total concentration of lysophosphatidic acid species.

7. The method of claim 5, wherein the compound is

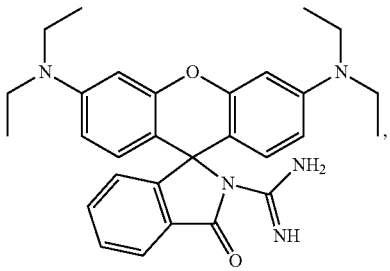 [SMILES: CCN(CC)c1ccc2c(c1)Oc1cc(N(CC)CC)ccc1C21c2ccccc2C(=O)N1C(=N)N]

and fluorescence intensity is measured at 570 nm.

8. The method of claim 6, wherein the condition is cancer, cardiovascular disease, platelet aggregation, ischemia perfusion injury, neuropathic pain, a neuropsychiatric disorder, a reproductive disorder, or fibrosis.

9. A kit for detecting and quantifying lysophosphatidic acid, comprising at least one compound according to claim 1.

10. The kit of claim 9, wherein the compound is

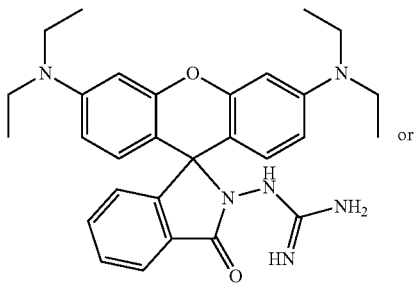

or

-continued

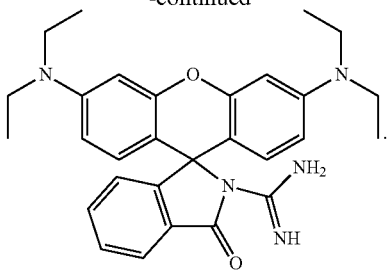

11. The method of claim 6, wherein the condition is ovarian cancer.

12. The method of claim 6, wherein extracting lysophosphatidic acid species from the sample comprising plasma or serum further comprises:
  combining the sample comprising plasma or serum with a solvent comprising a $C_1$-$C_{10}$ alkyl alcohol and chloroform to form a mixture;
  separating organic and aqueous layers of the mixture;
  extracting the aqueous layer with a buffer at neutral pH to form an extracted aqueous phase;
  mixing the extracted aqueous phase with chloroform;
  separating chloroform from the extracted aqueous phase to form a washed aqueous phase;
  adding phosphoric acid to the washed aqueous phase to form an acidified aqueous phase;
  loading the acidified aqueous phase onto a solid-phase extraction (SPE) cartridge including a stationary phase comprising silica derivatized with hydrocarbon chains;
  flowing water and subsequently chloroform through the SPE cartridge;
  drying the SPE cartridge; and
  flowing a $C_1$-$C_{10}$ alkyl alcohol through the SPE cartridge, thereby eluting lysophosphatidic acid species in the $C_1$-$C_{10}$ alkyl alcohol from the SPE cartridge.

13. The compound of claim 1, wherein $R^{13}$ is NH.

* * * * *